(12) United States Patent
Laub

(10) Patent No.: US 6,569,416 B1
(45) Date of Patent: *May 27, 2003

(54) COMPOSITIONS CONTAINING SYNTHETIC SOIL-EXTRACT MATERIALS AND MEDICAMENTS BASED THEREON

(75) Inventor: Richard J. Laub, Newport Beach, CA (US)

(73) Assignee: Lamb Biochemicals Corp., Newport Beach, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/345,865

(22) Filed: Jul. 1, 1999

Related U.S. Application Data

(62) Division of application No. 08/798,329, filed on Feb. 10, 1997, now Pat. No. 5,945,446.

(51) Int. Cl.[7] ............... A61K 31/74; A61K 39/385; A61K 31/35

(52) U.S. Cl. ............... 424/78.02; 424/195.11; 514/456

(58) Field of Search ............... 424/78.02, 683

(56) References Cited

U.S. PATENT DOCUMENTS

| | | | |
|---|---|---|---|
| 4,921,840 A | | 5/1990 | Seubert et al. |
| 4,999,202 A | * | 3/1991 | Cronje et al. ............... 424/683 |
| 5,284,651 A | | 2/1994 | Riede et al. |

FOREIGN PATENT DOCUMENTS

| | | |
|---|---|---|
| DE | 3830333 C1 | 3/1990 |
| DE | 0537430 A1 | 4/1993 |
| DE | 41 34 378 A1 | 4/1993 |
| EP | 0119768 A1 | 9/1984 |

OTHER PUBLICATIONS

"Selective Inhibitory Activity of Polyhydroxycarboxylates Derived from Phenolic Compounds Against Human Immunodeficiency Virus Replication"—Dominique Schols, Peter Wutzler, Renate Kloching, Bjorn Helbig, and Erik De Clercq Journal of Acquired Immune Deficiency Syndromes; 4:677–685, 1991 Raven Press, Ltd. New York.

"Sulfated Polysaccharides Are Potent and Selective Inhibitors of Various Enveloped Viruses, Including Herpes Simplex Virus, Cytomegalovirus, Vesicular Stomatitis Virus, and Human Immunodeficiency Virus"—Masanori Baba, Robert Snoeck, Rudi Pauwels, and Erik De Clercq Antimicrobial Agents and Chemotherapy, Nov. 1988, p. 1742–1745, vol. 32, No. 11.

"Comparison of Core Antigen (p24) Assay and Reverse Transcriptase Activity for Detection of Human Immunodeficiency Virus Type 1 Replication"—Sally Land, Fiona Beaton, Dale A. McPhee, and Ian D. Gust Journal of Clinical Microbiology, Mar. 1989, p. 486–489, vol. 27, No. 3.

WO 95/08335—PCT—Treatment Of HIV Infection With Humic Acid—Mar. 30, 1995.

(List continued on next page.)

Primary Examiner—Thurman K. Page
Assistant Examiner—Blessing Fubara
(74) Attorney, Agent, or Firm—Knobbe, Martens, Olson & Bear, LLP

(57) ABSTRACT

Compositions for treating viral and bacterial diseases are described. The compositions contain a synthetic soil phenolic polymeric material which contains sulfur, boron, alkaline earth, or transition metals but does not contain nitrogen. The synthetic materials may be synthetic humic acids or fulvic acids. The polymeric materials in the compositions are prepared by oxidizing one or more organic phenols in the presence of inorganic salts. Polymeric materials prepared from organic phenols having at least one carboxylic acid group are especially effective. The compositions can be injected, applied topically, ingested, inhaled, or applied as a suppository.

23 Claims, 3 Drawing Sheets

OTHER PUBLICATIONS

HealthGate Document—R. Ansorg et al.—Studies On The Antimicrobial Effect Of Natural And Synthetic Humic Acids—*Arzeimittelforschung* 1978, 28(12), pp. 2195–2198.

HealthGate Document—K.D. Thiel et al.—Comparison Of The In Vitro Activities Of Ammonium Humate And Of Enzymically Oxidized Chlorogenic And Caffeic Acids Against Type 1 And Type 2 Human Herpes Virus—*Pharmazie* 1981, 36(1), pp. 50–53.

HealthGate Document—H. Schultz—Investigations On The Viricidal Effects Of Humic Acids In Peat–Mull—*Dtsch Tierarztl Wochenschr* Jul. 1, 1965, 72(13), pp. 294–297.

HealthGate Document—R. Klocking et al.—Antiviral Properties Of Humic Acids—*Experientia* May 15, 1972, 28(5), pp. 607–608.

HealthGate Document—G. Sydow et al.—The Effect Of Phenolic Polymers On Retroviruses—*Pharmazie* Dec. 1986, 41(12), pp. 865–868.

R. Klocking and M. Sprossig—*Experientia* 1972 28(5)—pp. 607–608.

HealthGate Document—R. Klocking et al.—Antiviral Activity Of Phenolic Polymers Against Type 1 Herpesvirus Hominis—*Pharmazie* Aug. 1978, 33(8), p. 539.

HealthGate Document—F. Schiller et al.—Results Of An Oriented Clinical Trial Of Ammonium Humate For The Local Treatment Of Herpesvirus Hominus (HVH) Infections—*Dermatol Monatsschr* Jul. 1979, 165(7), pp. 505–509.

HealthGate Document—B Helbig et al.—Therapeutic Effect Of (E)–5–(2–Bromovinyl)–2'–Deoxyuridine, Caffeic Acid Oxidation Product, And Trisodiumphosphonoformate On Cutaneous Herpes Simplex Virus Type 1 Infection In Guinea Pigs—*J Med Virol* Nov. 1987, 23(3), pp. 303–309.

R. Klocking—Interaction Of Humic Acids And Humic–Acid–Like Polymers With Herpes Simplex Virus Type 1—*Humanic Substances in the Aquatic and Terrestrial Environment*, Berlin 1991, pp. 408–412.

HealthGate Document—In Vitro Studies Of The Antiviral Activity Of Enzymatically Oxidized O–Diphenolic Compounds Against Herpes Simplex Virus Type 1 And 2—*Zentralbl Bakterios (Orig. A)* Mar. 1979, 234(2), pp. 159–169.

HealthGate Document—K.D. Thiel et al.—In Vitro Studies Of The Antiviral Activity Of Ammonium Humate Against Herpes Simplex Virus Type 1 And Type 2—*Zentralbl Bakteriol (Orig. A)* Nov. 1977, 239(3), pp. 304–321.

HealthGate Document—K.D. Thiel et al.—Comparison Of The In Vitro Activities Of Ammonium Humate And Of Enzymically Oxidized Chlorogenic And Caffeic Acids Against Type 1 and Type 2 Human Herpes Virus—*Pharmazie* 1981, 36(1), pp. 50–53.

HealthGate Document—K.D. Thiel et al.—Antiviral Activity Of Enzymatically Oxidized Caffeic Acid Against Herpesvirus Hominis Type 1 And Type 2—*Acta Virol* May 1983, 27(3), pp. 200–208.

HealthGate Document—K.D. Thiel et al.—Antiviral Effect Of Enzymatically And Nonenzymatically Oxidized Caffeic And Hydrocaffeic Acids Against Herpesvirus Hominis Type 1 And Type 2 In Vitro—*Pharmazie* Nov. 1984, 39(11), pp. 781–782.

M. Cushman et al.—Preparation And Anti–Hiv Activities Of Aurintricarboxylic Acid Fractions And Analogues: Direct Correlation Of Antiviral Potency With Molecular Weight—*Journal of Medicinal Chemistry* 1991, 34(1), pp 329–337.

M. Cushman et al.—Synthesis And Anti–HIV Activities Of Low Molecular Weight Aurintricarboxylic Acid Fragments And Related Compounds—*Journal of Medicinal Chemistry* 1991, vol. 34, pp. 337–342.

HealthGate Document—D. Schols et al.—Selective Inhibitory Activity Of Polyhydroxcarboxylates Derived From Phenolic Compounds Against Human Immunodeficiency Virus Replication—*J. Acquir Immune Defic Syndr* 1991, 4(7), pp. 677–685.

S. Loya et al.—Hexaprenoid Hydroquinones, Novel Inhibitors Of The Reverse Transcriptase Of Human Immunodeficiency Virus Type 1—*Journal of Natural Products* Dec. 1993, 56(12), pp. 2120–2125.

J. Schneider et al.—Inhibition Of HIV–1 In Cell Culture By Synthetic Humate Analogues Derived From Hydroquinone: Mechanism Of Inhibition—*Virology* 1996, 218(2), pp. 389–395.

HealthGate Document—R. Mentel et al.—Effectiveness Of Phenol Body Polymers Against Influenza Virus A/Krasnodar/101/59/H2N2—*Biomed Biochem Acta* 1983, 42(10), pp. 1353–1356.

HealthGate Document—J. Hills et al.—Inhibition Of Several Strains Of Influenza Virus Type A And B By Phenolic Polymers—*Biomed Biochem Acta* 1986, 45(9), pp. 1173–1179.

A. Jankowski et al.—A Randomized, Double–Blind Study On The Efficacy Of Tolpa Torf Preparation (TTP) In the Treatment Of Recurrent Respiratory Tract Infections—*Arch Immunol Ther Exp (Warsz)* 1993, 41(1), pp. 95–97.

R. Klocking et al.—Title?—*Pharmazie* 1977, 32, p. 297.

HealthGate Document—R. Klocking et al.—Preparation, Characterization And Antiviral Activity Of Phenolic Polyers. 2. Antiviral Activity Of Phenolic Polymers (Proceedings)—*Pharmazie* May 1979, 34(5–6), pp. 293–294.

HealthGate Document—R. Mentel et al.—Effectiveness Of Phenol Body Polymers Against Influenza Virus A/Krasnodar/101/59/H2N2—*Biomed Biochim Acta* 1983, 42(10), pp. 1353–1356.

HealthGate Document—H.P. Klocking et al.—Effect Of Phenol Ring Polymers On The Release Of Plasminogen Activators—*Farmakol Toksikol* Jan.–Feb. 1984, 47(1), pp. 93–95.

HealthGate Document—K.D. Thiel et al.—Antiviral Effect Of Enzymatically And Nonezymatically Oxidized Caffeic And Hydrocaffeic Acids Against Herpesvirus Hominis Type 1 And Type 2 In Vitro—Pharmazie. 39: 11, Nov. 1984, 781–782.

J. Hills—Hemmung Ausgewahlter Influenzavirusstamme Der Typen A And B Durch Phenolkorperpolymerisate—*Biomed Biochim Acta* 1986, 45(9), pp. 1173–1179.

HealthGate Document—B. Helbig et al.—Therapeutic Effect Of (E)–5–(2–Bromovinyl)–2–Deoxyuridine, Caffeic Acid Oxidation Product, And Trisodiumphosphonoformate On Cutaneous Herpes Simplex Virus Type 1 Infection In Guinea Pigs—*J Med Virol* Nov. 1987, 23(3), pp. 303–309.

K. I. Hanninen et al.—Synthesis And Characterization Of Humic Acid–Like Polymers—*The Science of the Total Environment* 1987, 62, pp. 201–210.

R. Klocking et al.—Interaction Of Humic Acids And Humic–Acid–Like Polymers With Herpes Simplex Virus Type 1 *Humic Substances in the Aquatic and Terrestrial Environment* New York—Springer–Verlag 1989, pp. 407–412.

HealthGate Document—C. Schewe et al.—Lipoxygenase–Inhibitory Action Of Antiviral Polymeric Oxidation Products Of Polyphenols—*Biomed Biochem Acta* 1991, 50(3), pp. 299–305.

D. Schols et al.—Selective Inhibitory Activity Of Polyhydroxycarboxylates Derived From Phenolic Compounds Against Human Immunodeficiency Virus Replication—*Journal of Acquired Immune Deficiency Syndromes* 1991, 4(7), pp. 677–685.

M. Cushman et al.—Preparation And Anti–Hiv Activities Of Aurintricarboxylic Acid Fractions And Analogues Direct Correlation Of Antiviral Potency With Molecular Weight—*Journal of Medicinal Chemistry* 1991, 34(1), pp 329–337.

M. Cushman et al.—Synthesis And Anti–Hiv Activities Of Low Molecular Weight Aurintricarboxylic Acid Fragments And Related Compounds—*Journal of Medicinal Chemistry* 1991, 34(1), pp. 337–342.

HealthGate Document—M. Robert–Gero et al.—Biochemical Study Of Humus Action Of A Proteolytic Enzyme On Natural And Synthetic Humic Polymers And Those Of Microbial Origin—*Ann Inst Pasteur (Paris)* Dec. 1967, 113(6), pp. 903–909.

HealthGate Document—M. Jakubiec et al.—Comparison Of The Effect Of Natural And Synthetic Humates And Edta On The Growth Of *Escherichia coli*—**Abstract not available.

HealthGate Document—R. Ansorg et al.—Studies On The Antimicrobial Effect On Natural And Synthetic Humic Acids—*Arzneimittelforschung* 1978, 28(12, pp. 2195–2198.

HealthGate Document—J. Pommery et al.—SOS Chromotest Study Concerning Some Appreciation Criteria Of Humic Substances' Genotoxic Potency—*Mutat Res* Jun. 1989, 223(2), pp. 183–189.

HealthGate Document—Department of Biochemistry et al.—Humic Acid: Inhibitor of Plasmin—*Sci Total Environ* Apr. 1992, 114, pp. 135–139.

HealthGate Document—K. Wiegleb et al.—The Use Of The Het–Cam Test For The Determination Of The Irritating Effects Of Humic Acids—*DTW Dtsch Tierarztl Wochenschr* Oct. 1993, 100(10), pp. 412–416.

HealthGate Document—H.L. Yang et al.—Humic Acid Induces Expression Of Tissue Factor By Cultured Endothelial Cells: Regulation By Cytosolic Calcium And Protein Kinase C—*Thromb Haemost* Mar. 1994, 71(3), pp. 325–330.

HealthGate Document—W. Seffner—Subchronic Application Of Humic Acids And Associated Compounds Provokes Histological Changes Of Goitre In The Rat—*Exp Toxicol Pathol* Jan. 1995, 47(1), pp. 63–70.

HealthGate Document—J. Schneider—Inhibition Of Hiv–1 Cell Culture By Synthetic Humate Analogues Derived From Hydro Mechanism Of Inhibition—*Virology* Apr. 15, 1996, 218(2), pp. 389–395.

Hassett et al. 109 CA: 539 LLY, 1988.

Shindo 117 CA 52663x, 1992.

* cited by examiner ized in quantitative inhibition studies. Natural humic materials, on the other hand, possess ill-defined and variable structures that tend to confound attempts to understand the mechanisms by which these substances inhibit diverse viral and microbial pathogens.

COMPOSITIONS CONTAINING SYNTHETIC SOIL-EXTRACT MATERIALS AND MEDICAMENTS BASED THEREON

This application is a divisional of application Ser. No.: 08/798,329, filed Feb. 10, 1997 now U.S. Pat. No. 5,945,446.

FIELD OF THE INVENTION

This invention relates to synthetic soil extract substances comprised of phenolic polymers, to the procedures for the preparation thereof, to the processes for the purification and isolation as aqueous solutions or dried powders of the synthetic materials, to compositions and methods for employing these synthetic phenolic polymers for reducing or eliminating viral activity in blood products, anti-viral compositions for treating or preventing human or animal viral diseases and antimicrobial compositions for treating or preventing human or animal microbial diseases.

BACKGROUND OF THE INVENTION

Soil extract materials, particularly the classes of substances known collectively as "humus," "humics," "humic acid(s)," or "humates," have been widely used in a number of applications for many years, as reviewed by F. J. Stevenson, *Humus Chemistry. Genesis Composition Reactions*; New York: Wiley, 1964; and, more recently, by A. Piccolo, *Humic Substances in Terrestrial Ecosystems*; New York: Elsevier, 1996.

Natural and synthetic soil extracts have already been used extensively in horticultural and related industries, particularly as soil enhancement as well as soil remediation agents. In addition, natural and synthetic soil extracts have been employed as additives in organic gardening and landscaping; and in fresh-water aquaria. Some medicinal benefits have also been claimed for both synthetic- and naturally-occurring soil extract substances.

R. H. Faust, in a paper presented at the *Conference of the International Federation of Organic Agriculture Movements; Copenhagen, Denmark: October,* 1996; P2, 20, has documented the benefits of humates in agriculture. In general, it has been found that humic materials can stimulate plant growth, including crop yield, by about 10–30%.

Soil extracts, and humic acid in particular, chelate a variety of metals. As a result, humic materials have been employed in soil remediation to remove heavy-metal contamination, as reported by M. A. Rashid, *Soil Sci.* 1971, 111, 298–306. Humic acid has also been used to enhance the removal of aromatic hydrocarbons from aquifers contaminated with petroleum products: H. Xu, S. Lesage, L. Durham, and K. Novakowski, in *Proceedings of the Fourth Annual Symposium on Groundwater and Soil Remediation; Calgary Alberta: Sep.* 21–23, 1994; 635–646; S. Lesage, H. Xu, K. S. Novakowski, S. Brown, and L. Durham, in *Proceedings of the Fifth Annual Symposium on Groundwater and Soil Remediation*; Toronto, Ontario: Oct. 2–6, 1995.

Humate materials have been used as poultry feed additives. Adding humate materials to the fodder of broiler chickens increases the yield mass on average by 5–7%, and also provides for a 3–5% gain in poultry safety: L. M. Stepchenko, L. V. Zhorina, and L. V. Kravtsova, *Biol. Nauki* 1991, 10, 90–95.

T. A. Huck, N. Porter, and M. E. Bushell, *J. Gen. Microbiol.* 1991, 137(10), 2321–2329, have reported that soil isolates are effective media additives for the production of antibiotics, and that the extent of microbial growth stimulation can be quite large depending upon the species, the culture medium, and the environment. The use of selected batches of soil lignite humate as culture media for isolating thermophilic Campylobacter species extracts has also been documented by K. Weinrich, K. Winkler, and E. Heberer, *DTW Dtsch. Tierarztl Wochenschr.* 1990, 97(12), 511–515. In addition, B. Grunda, *Zentralbl. Bakteriol. Parasitenkd. Infektionskr. Hyg.* 1970, 125(6), 584–593, has described the effects of humic acid on the count of soil microorganisms in culture.

Humates have long been used as folk remedies for a wide variety of illnesses (F. K. Achard, *Crells Chem. Ann.* 1786, 11, 391–403), as recounted by T. D. Lotosh, *Biol. Nauki* 1991, 10, 99–103.

Humic acids isolated from peat exhibited significant efficacy for adhesions when tested on female rats that had standardized lesions placed on both uterine horns and the peritoneum of the anterior abdominal wall: M. Mesrogli, D. H. Maas, B. Mauss, S. Plogmann, W. Ziechmann, and J. Schneider, *Zentralbl. Gynakol.* 1991, 113(10), 583–590.

The ability of natural humic acid to affect anaphylactic sensitization and mast cell secretory function has been established by J. Wyczolkowska, T. Michon, Z. Slusarczyk, B. Kolago, and C. Maslinski, *Acta Pol. Pharm.* 1993, 50(6), 475–480. Humic substances in doses of 20 and 50 milligrams per kilogram body weight reduced histamine release from mouse peritoneal mast cells challenged with anti-IgE or concanavalin A in vitro.

Humic substances, including peats and sodium humates, are known to exhibit anti-inflammatory properties: M. Kuhnert, V. Fuchs, and S. Golbs, *Arch. Exp. Veterinarmed.* 1982, 36(2), 169–177; S. B. Ye, J. Y. Chen, and Z. X. Zeng, *Ssu Chuan I Hsueh Yuan Hsueh Pao* 1985, 16(2), 127–129. Inflammatory states of the cervix, especially cervical erosion (known generally as cervicitis), can be treated with humic preparations: J. Woyton, M. Gabrys, T. Bielanow, M. Zimmer, J. Sokalski, R. Geneja, and M. Zborowski, *Arch. Immunol. Ther. Exp. (Warsz)* 1993, 41(1), 99–103.

Humic substances have been known to exhibit antimicrobial properties. Species for which natural as well as synthetic humic substances have been shown to be inhibitory include *C. albicans, Ent. cloacae, Prot. vulgaris, Ps. aeruginosa, S. typhimurium, St. aureus, St. epidermidis, Str. pyogenes* (R. Ansorg and W. Rochus, *Arzneimittelforschung* 1978, 28(12), 2195–2198; *E. coli* and *Str. faecalis* were not affected), and *Str. mutans* (*sobrinus*) (Y. Nakamura, H. Kuwashima, S. Aoki, and T. Masuhara, *Shika Kiso Igakkai Zasshi* 1989, 31(3), 329–332). Broadly speaking, concentrations in the range 50–2000 parts per million (ppm) are usually effective, yet are not cytotoxic: K. D. Thiel, B. Helbig, R. Klocking, P. Wutzler, M. Sprossig, and H. Schweizer, *Pharmazie* 1981, 36(1), 50–53.

Humic substances have long been known to exhibit anti-viral properties (H. Schultz, *Dtsch. Tierarztl. Wochenschr.* 1962, 69, 613; 1965, 72(13), 294–297; R. Klocking and M. Sprossig, *Experientia* 1972, 28(5), 607–608), particularly retroviruses (G. Sydow, V. Wunderlich, R. Klocking, and B. Helbig, *Pharmazie* 1986, 41(12), 865–868). Viral pathogens for which soil-extract materials have been shown to be effective include in particular Coxsackie virus A9 (Griggs-Baylor) (R. Klocking and M. Sprossig, *Experientia* 1972, 28(5), 607–608), herpes simplex virus type 1 (B. T. Rouse (Ed.), Herpes Simplex Virus; Berlin: Springer-Verlag, 1992; R. Klocking, K. D. Thiel, P. Wutzler, B. Helbig, and P. Drabke, *Pharmazie* 1978, 33(8), 539; F. Schiller, R.

Klocking, P. Wutzler, and I. Farber, *Dermatol. Monatsschr.* 1979, 165(7), 505–509; B. Helbig, A. Sauerbrei, R. Klocking, P. Wutzler, N. Wicht, U. Wiedemann, and G. Herrmann, *J. Med. Virol.* 1987, 23(3), 303–309; R. Klocking and B. Helbig, in *Humic Substances in the Aquatic and Terrestrial Environment*; Berlin: Springer-Verlag, 1991; 407–412;) and type 2 (anon. *Zentralbl. Bakteriol* [*Orig. A*] 1976, 234(2), 159–169; K. D. Thiel, R. Klocking, H. Schweizer, and M. Sprossig, *Zentralbl. Bakteriol* [*Orig. A*] 1977, 239(3), 304–321; K. D. Thiel, B. Helbig, R. Klocking, P. Wutzler, M. Sprossig, and H. Schweizer, *Pharmazie* 1981, 36(1), 50–53; K. D. Thiel, B. Helbig, M. Sprossig, R. Klocking, and P. Wutzler, *Acta Virol.* 1983, 27(3), 200–208; K. D. Thiel, P. Wutzler, B. Helbig, R. Klocking, M. Sprossig, and H. Schweizer, *Pharmazie* 1984, 39(11), 781–782); human immunodeficiency virus (HIV) (M. Cushman, P. Wang, S. H. Chang, C. Wild, E. De Clercq, D. Schols, M. E. Goldman, and J. A. Bowen, *J. Med Chem.* 1991, 34(1), 329–337; M. Cushman, S. Kanamathareddy, E. De Clercq, D. Schols, M. E. Goldman, and J. A. Bowen, *J. Med Chem.* 1991, 34(1), 337–342; D. Schols, P. Wutzler, R. Klocking, B. Helbig, and E. De Clercq, *J. Acquir. Immune Defic. Syndr.* 1991, 4(7), 677–685; S. Loya, R. Tal, A. Hizi, S. Issacs, Y. Kashman, and Y. Loya, *J. Nat. Prod* 1993, 56(12), 2120–2125; J. Schneider, R. Weis, C. Manner, B, Kary, A. Werner, B. J. Seubert, and U. N. Riede, *Virology* 1996, 218(2), 389–395; influenza virus type A (Krasnodar/101/59/H2N2) (R. Mentel, B. Helbig, R. Klocking, L. Dohner, and M. Sprossig, *Biomed. Biochim. Acta* 1983, 42(10), 1353–1356); and type B (J. Hils, A. May, M. Sperber, R. Klocking, B. Helbig, and M. Sprossig, *Biomed. Biochim. Acta* 1986, 45(9), 1173–1179); as well as other respiratory tract infectious agents (A. Jankowski, B. Nienartowicz, B. Polanska, and A. Lewandowicz-Uszynska, *Arch. Immunol. Ther. Exp.* (Warsz) 1993, 41(1), 95–97).

The mechanism whereby humic substances inhibit the cytopathicity of a number of viruses has been studied in some detail. It is thought that the materials prevent viral replicating by sorbing onto the viral envelope protein (gp120SU in the case of HIV) and thereby blocking the sorption of viral particles to cell surfaces: K. D. Thiel, R. Klocking, H. Schweizer, and M. Sprossig, *Zentralbl. Bakteriol.* [*Orig. A*] 1977, 239(3), 304–321; D. Schols, P. Wutzler, R. Klocking, B. Helbig, and E. De Clercq, *J. Acquir. Immune Def. Syndr.* 1991, 4(7), 677–685; anon., *Fortschr. Med.* 1995, 113(7), 10; J. Schneider, R. Weis, C. Manner, B. Kary, A. Werner, B. J. Seubert, and U. N. Riede, *Virology* 1996, 218(2), 389–395. Extracellular interception of pathogens by chemical agents that bind to them is a well-known means of immunological defense (D. M. Shankel, S. Kuo, C. Haines, and L. A. Mitscher, in *Antimutagenesis and Anticarcinogenesis Mechanisms III*; G. Bronzetti, H. Hayatsu, S. De Flora, M. D. Waters, and D. M. Shankel (Eds.); New York: Plenum, 1993; 65–74). Such materials might well be termed "despathogens," following the terminology proposed by T. Kada and K. Shimoi, *Bioessays* 1987, 7, 113–116, regarding "desmutagens."

It has been reported that heat treatment of humic acids at 120 degrees Centigrade for 15 minutes does not alter their inhibitory effect on mutagens: T. Sato, Y. Ose, and H. Nagase, *Mutat. Res.* 1986, 162(2), 173–178; T. Sato, Y. Ose, H. Nagase, and K. Hayase, *Sci. Total Environ.* 1987, 62(4), 305–310). That is, humic acids can be sterilized by autoclaving.

A direct comparison of enzymatic- with nonenzymatic-synthesized humic acid has shown that the latter is about a factor of ten more effective than the former for the treatment of herpes types 1 and 2: K. D. Thiel, P. Wutzler, B. Helbig, R. Klocking, M. Sprossig, and H. Schweizer, *Pharmazie* 1984, 39(11), 781–782.

Implanted bovine calcium hydroxyapatite is highly osteoconductive, and serves the host tissue as a "guideline" for the deposition of newly developing bone tissue. However, while it is well tolerated, it is resorbed only very slowly. Impregnation of the bovine hydroxyapatite with synthetic humic acid measurably stimulates the resorption process.

There is extensive covalent as well as hydrogen bonding of humic substances to collagen fibers (with undoubted crosslinking as well), as determined by x-ray diffraction analysis: U. N. Riede, I. Jonas, B. Kirn, U. H. Usener, W. Kreutz, and W. Schlickewey, *Arch. Orthop. Trauma Surg.* 1992, 111(5), 259–264. Tendon strength is thereby increased by as much as 75 percent.

Natural as well as synthetic humic acids have been found to stimulate the phagocytic and bactericidal activity of granulocytes in humans at dose levels of 100–300 milligrams per day over a 14-day testing period: U. N. Riede, G. Zeck-Kapp, N. Freudenberg, H. U. Keller, and B. Seubert, *Virchows Arch. B Cell Pathol. Incl. Mol. Pathol.* 1991, 60(1), 27–34; M. Kowalska, A. Denys, and J. Bialek, *Acta Pol. Pharm.* 1993, 50(4–5), 393–395. Of additional interest is the finding that dose levels of 600 milligrams per day caused only a transient and insignificant increase of phagocytic and bactericidal properties of the granulocytes.

The influence of natural as well as synthetic humic acids on haemostasis has been studied: H. P. Klocking, *Arch. Toxicol. Suppl.* 1991, 14, 166–169; W. Buczko, B. Malinowska, M. H. Pietraszek, D. Pawlak, and E. Chabielska, *Acta Pol. Pharm.* 1993, 50(6), 507–511. It was found that humic acid in dose levels of 100–300 milligrams per kilogram body weight had no effect on bleeding time, clotting time, thrombin time, prothrombin time, kaolin-kephalin time, euglobulin lysis time, the concentration of fibrinogen, the platelet count, or ADP-induced platelet aggregation.

Various synthetic humic acids have been found to inhibit strongly the activity of purified lipoxygenase of rabbit reticulocytes, whereas prostaglandin H synthase of sheep vesicular gland is only weakly inhibited: C. Schewe, R. Klocking, B. Helbig, and T. Schewe, *Biomed. Biochim. Acta* 1991, 50(3), 299–305. The most effective humic acids were those derived from caffeic acid, 2,5-dihydroxytoluene, and 3,4-dihydroxytoluene.

The effect of natural humic acid on the regenerative response of liver tissue has been examined in rats submitted to two-thirds hepatectomy. The results were thought to be two-fold in nature. First, the short-term application of humic acid at a dose of 20 milligrams per kilogram body weight per day inhibited ornithine decarboxylase activity, as well as caused a decrease in spermidine formation and DNA and RNA, resulting in an overall decrease in liver restitution. In contrast, long-term application of humic acid resulted in the stimulation of ornithine decarboxylase, an increase in spermidine and histamine as well as RNA and DNA levels, and in overall liver mass. The effects might be due at least in part to the humic-acid inhibition of polyamine biosynthesis: C. Maslinksi, W. A. Fogel, and W. Andrzejewski, *Acta Pol. Pharm.* 1993, 50(4–5), 413–416.

Humic as well as fulvic acids extracted from peat have been shown to stimulate respiration in rat liver mitochondria when present at concentrations of 40–360 micrograms per milliliter. Humic substances at concentrations of 40–400 micrograms per milliliter also increased the efficiency of oxidative phosphorylation in mitochondria in vitro, particularly after contact periods of over 1 hour: S. A. Visser, *Sci. Total Environ.* 1987, 62(4), 347–354.

Natural, synthetic, and commercial humic acids all have the ability to inhibit human plasmin activity: F. J. Lu and Y. S. Lee, *Sci. Total Environ.* 1992, 114(4), 135–139. Thus, at a concentration of 20 micrograms per milliliter, each resulted respectively in residual plasmin activities of 70, 93, and 40 percent. Synthetic humic acids fabricated from caffeic acid and 3,4-dihydroxyphenylacetic acid have also been found to raise the activity of plasminogen activator in isolated vascular preparations of pig ear (H. P. Klocking, R. Klocking, and B. Helbig, *Farmakol. Toksikol* 1984, 47(1), 93–95).

Peat-derived natural humic acids have been found to inhibit the hydrolysis of N-acetyl-L-tyrosine ethyl ester and N-benzoyl-L-leucine methyl ester by alpha-chymotrypsin as well as by subtilisin: Sh. Zh. Zhorobekova and K. A. Kydralieva, *Biol. Nauki* 1991, 10, 151–154.

Sodium humate has been found to increase the lifespan of mongrel rats exposed to lethal doses of $^{60}Co$ -radiation, as reported by G. G. Pukhova, N. A. Druzhina, L. M. Stepchenko, and E. E. Chebotarev, *Radiobiologiia* 1987, 27(5), 650–653.

It has been found that naturally-occurring humic acid preparations can stimulate the production of cytokines, including interferon-gamma, interferon-alpha, and tumor necrosis factor-alpha (A. D. Inglot, J. Zielinksa-Jenczylik, and E. Piasecki, *Arch. Immunol. Ther. Exp. (Warsz)* 1993, 41(1), 73–80); and interferon-beta (Z. Blach-Olszewska, E. Zaczynksa, E. Broniarek, and A. D. Inglot, *Arch. Immunol. Ther. Exp. (Warsz)*, 1993, 41(1), 81–85).

Histopathological and ultrastructural studies have shown that naturally-occurring humic acids can cause morphological changes characteristic of thymus activity stimulation: J. A. Madej, J. Kuryszko, and T. Garbulinski,*Acta Pol. Pharm.* 1993, 50(4–5), 397–404.

It has been shown that incubation of cultured human umbilical vein endothelial cells either with natural or synthetic humic acid results in an enhanced cell surface expression of tissue factor activity. There are also changes in intracellular divalent calcium levels: H. L. Yang, F. J. Lu, S. L. Wung, and H. C. Chiu, *Thromb. Haemost.* 1994, 71(3), 325–330.

Natural humic acid administered prophylactically to rats can decrease significantly the amount of gastric mucosa damage induced with ethanol. Humic acid also significantly accelerates the healing process of experimental-induced gastric and duodenal ulcers: T. Brzozowski, A. Dembinski, and S. Konturek,*Acta Pol. Pharm.* 1994, 51(1), 103–107.

Humic acids have also been employed as veterinary medicine therapies, as described and discussed by M. Kuhnert, V. Fuchs, H. Knauf, and U. Knoll, *Arch. Exp. Veterinarmed.* 1985, 39(3), 344–349; and by M. Kuhnert, V. Fuchs, and S. Golb, *Dtsch. Tierarztl. Wochenschr.* 1989, 96(1), 3–10. For example, H. Schultz, *Dtsch. Tierarztl. Wochenschr.* 1962, 69, 613; 1965, 72(13), 294–297, successfully employed peat mull to prevent the transmission of foot and mouth disease in pigs.

The pharmacokinetics of sodium humate in chickens have been studied extensively by J. Hampl, I. Herzig, and J. Vlcek, *Vet. Med. (Praha),* 1994, 39(6), 305–313. Free or liposome-encapsulated sodium humate was administered to chickens intracardially, orally, or subcutaneously and a number of pharmacokinetic parameters were then determined. The blood clearance of liposome-encapsulated sodium humate was higher than that of free sodium humate regardless of the manner of administration. On the other hand, the elimination half-life was longer after extravascular than after intracardial administration. Maximal drug concentration values indicated that the penetration of sodium humate from the injection site into blood circulation is very slow. Biological availability of sodium humate also depended on the method of administration and dosage form. Aside from intracardial administration, the highest bioavailability was found after subcutaneous administration of free sodium humate. Synthetic humic acid has been found to penetrate the dermis very quickly from a 1 percent water/oil emulsion, and to then form a reservoir in the horny layer: W. Wohlrab, B. Helbig, R. Klocking, and M. Sprossig, *Pharmazie* 1984, 39(8), 562–564. Also, about 30 minutes after external application, concentrations of 1–3 percent of the total quantity applied are achieved, which percentage remains essentially unchanged thereafter.

The toxicity of naturally-occurring humic acids is remarkably low (K. D. Thiel, B. Helbig, R. Klocking, P. Wutzler, M. Sprossig, and H. Schweizer, *Pharmazie* 1981, 36(1), 50–53; U. N. Riede, 1. Jonas, B. Kirn, U. H. Usener, W. Kreutz, and W. Schlickewey, *Arch. Orthop. Trauma Surg.* 1992, 111(5), 259–264; H. Czyzewska-Szafran, Z. Jastrzebski, D. Soltysiak-Pawluczuk, M. Wutkiewicz, A. Jedrych, and M. Remiszewska, *Acta Pol. Pharm.* 1993, 50(4–5), 373–377; H. L. Yang, F. J. Lu, S. L. Wung, and H. C. Chiu, *Thromb. Haemost.* 1994, 71(3), 325–330). [Cytotoxic effects of antiviral substances, including humic acids, are usually evaluated via biological (viability and alterations of cell morphology) and biochemical testing methods ($^{51}Cr$ release), as described by K. D. Thiel, U. Eichhorn, H. Schweizer, and R. Klocking, *Arch. Toxicol. Suppl.* 1980, 4, 428–430.] The cytotoxicity ($CD_{50}$) of a naturally-occurring humic acid for human peripheral blood leukocytes (PBL) was found to be 1–9 milligrams per milliliter. In addition, J. Schneider, R. Weis, C. Manner, B. Kary, A. Werner, B. J. Seubert, and U. N. Riede, *Virology* 1996, 218(2), 389–395, reported that the cytotoxicity of a synthetic humic acid prepared from hydroquinone for MT-2 cells was approximately 600 micrograms per milliliter. It has also been found that medicaments prepared from humic acids isolated from naturally-occurring soil materials are neither carcinogenic (Syrian hamster embryo cell transformation test: J. Koziorowska and E. Anuszewska,*Acta Pol. Pharm.* 1994, 51(1), 101–102) nor mutagenic (T. Sato, Y. Ose, and H. Hagase, *Mutat. Res.* 1986, 162(2), 173–178; V. M. Sui, A. I. Kiung, and T. I. Veidebaum, *Vopr. Kurortol. Fiozioter. Lech. Fiz. Kult.* 1986, 2(3–4), 34–37; J. Koziorowska, B. Chlopkiewicz, and E. Anuszewska, *Acta Pol. Pharm.* 1993, 50(4–5), 379–382). Prenatal (S. Golbs, V. Fuchs, M. Kuhnert, and C. Polo, *Arch. Exp. Veterinarmed.* 1982, 36(2), 179–185) and embryotoxic and teratogenic effects (T. Juszkiewicz, M. Minta, B. Wlodarczyk, B. Biernacki, and J. Zmudzki,*Acta Pol. Pharm.* 1993, 50(4–5), 383–388) are also not observed with humic preparations at daily dose levels from 5–50 milligrams per kilogram body weight. Topical preparations are tolerated even better (V. V. Soldatov and M. N. Cherepanova, *Vopr. Kurortol. Fizioter. Lech. Fiz. Kult.* 1970, 35(3), 256–259; H. Czyzewska-Szafran, Z. Jastrzebski, D. Soltysiak-Pawluczuk, M. Wutkiewicz, A. Jedrych, and M. Remiszewska, *Acta Pol. Pharm.* 1993, 50(4–5), 373–377) when applied dermally in aqueous solution in amounts as high as 10 percent weight-by-volume (K. Wiegleb, N. Lange, and M. Kuhnert, *Dtsch. Tierarztl. Wochenschr.* 1993, 100(10), 412–416).

Soil extracts, including humics, are quite complex mixtures of organic and inorganic polymeric compounds whose composition varies widely depending upon the source of the soil and the method(s) of extraction and subsequent treatment: D. Vaughan and R. E. Malcolm, *Plant Soil Sci.* 1985, 16, 1–443 (see also N. Senesi, Y. Chen, and M. Schnitzer, *Soil Biol. Biochem.* 1977, 9, 397–403).

Techniques used for the chemical characterization of soil extracts, including humics, have included capillary electrophoresis (S. Pompe, K. Heise, and H. Nitsche, *J. Chromatogr. A,* 1996, A723(1), 215–218), ultracentrifugation (R. S. Cameron, B. K. Thornton, R. S. Swift, and A. M. Posner, *J. Soil Sci.* 1972, 23(4), 394–408; A. E. Wilkinson, J. J. Higgo, and M. N. Jones, *Biochem. Soc. Trans.* 1991, 19(4), 414S), electron paramagnetic resonance and infrared spectroscopy (G. Tollin and C. Steelink, *Biochim. Biophys. Acta,* 1966, 112(2), 377–379), various solvent and other fractionation methods (R. S. Cameron, B. K. Thornton, R. S. Swift, and A. M. Posner, *J. Soil Sci.* 1972, 23(4), 394–408; C. E. Clapp, M. H. Hayes, and R. S. Swift, *Agricultural Research Service Report Number* 0000042025; M. H. Hayes, R. L. Malcolm, and C. E. Clapp, *Agricultural Research Service Report Number* 0000042035; I. Csiky, G. Marko-Varga, and J. A. Jonsson, *Anal Chim. Acta* 1985, 178, 307–312; J. A. Amador, P. J. Milne, C. A. Moore, and R. G. Zika, *Mar. Chem.* 1990, 29, 1–17), gas chromatography (I. Arsenie, H. Boren, and B. Allard, *Sci. Total Environ.* 1992, 116(3), 213–220), gas chromatography-mass spectrometry (H.-R. Schulten and M. Schnitzer, *Soil Sci.* 1992, 153(3), 205–224; G. Chiavari, G. Torsi, D. Fabbri, and G. C. Galletti, *Analyst (London)* 1994, 119(6), 1141–1150), gel-permeation chromatography (B. Kosinkiewicz, *Acta Microbiol. Pol.* 1977, 26(4), 387–392; S. Mori, M. Hiraide, and A. Mizuike, *Anal. Chim. Acta* 1987, 193, 231–238), high-performance liquid chromatography (M. A. Curtis, A. F. Witt, S. B. Schram, and L. B. Rogers, *Anal. Chem.* 1981, 53, 1195–1199; K. Ravichandran, J. J. Lewis, I.-H. Yin, M. Koenigbauer, C. R. Powley, P. Shah, and L. B. Rogers, *J. Chromatogr.* 1988, 439, 213–226; J. Knuutinen, L. Virkki, P. Mannila, P. Mikkelson, J. Paasivirta, and S. Herve, *Wat. Res.* 1988, 22(8), 985–990, M. Susic and K. G. Boto, *J. Chromatogr.* 1989, 482(1), 175–187), mass spectrometry (H.-R. Schulten, G. Abbt-Braun, and F. H. Frimmel, *Environ. Sci. Technol.* 1987, 21(4), 349–357; C. Sorge, R. Mueller, P. Leinweber, and H. R. Schulten, *Fresenius' J. Anal. Chem.* 1993, 346 (6–9), 697–703; M. Remmler, A. Georgi, and F.-D. Kopinke, *Eur. Mass Spectrom.* 1995, 1(4), 403–407), nuclear magnetic resonance (F. J. Vila, H. Lentz, and H. D. Ludemann, *Biochem. Biophys. Res. Commun.* 1976, 72(3), 1063–1070; G. Almendros, R. Frund, F. J. Gonzalez-Vila, K. M. Haider, H. Knicker, and H. D. Ludemann, *FEBS Lett.* 1991, 282(1), 119–121), and polyacrylamide gel electrophoresis (R. Klocking, *J. Chromatogr.* 1973, 78, 409–416; L. P. Glazkova, V. S. Ulashchik, and F. A. Puntus, *Vopr. Kurortol. Fizioter. Lech. Fiz. Kult.* 1984, 2(2), 21–24).

Very many studies have been carried out on the structural characterization of soil extracts, including humic acid, by reductive degradation, as reviewed by L. B. Sonnenberg, Ph.D. Thesis, University of North Carolina at Chapel Hill, 1989: *Dissertation Services Order No.* 9007318. Models of humic structure based on the physicochemical properties of membranes have also been developed by R. L. Wershaw, *Environ. Health Perspect.* 1989, 83(11), 191–203. R. R. Engebretson and R. von Wandruszka, *Environ. Sci. Technol.* 1994, 28, 1934, have described efforts at characterizing the micro-organization of dissolved humic acids in terms of their secondary structure, that is, on the way in which these large molecules arrange themselves in three dimensions in solution. The molecules are thought to be dendritic, that is, are hyperbranched fractal-like structures that emanate somewhat like the spokes of a wagon-wheel from a central core, and which contain a large number of carboxyl and hydroxyl terminal groups: T. H. Mourey, S. R. Turner, M. Rubinstein, J. M. J. Frechet, C. J. Hawker, and K. L. Wooley, *Macromolecules* 1992, 25, 2401–2406. Cluster aggregates of humic acid have an average diameter of 700–1700 Angstroms; large clusters have a fractal dimension of 2.3: R. Osterberg and K. Mortensen, *Radiat. Environ. Biophys.* 1994, 33(3), 269–276.

Because humic substances are not chemically well-defined, the preparation of synthetic humic acids whose physicochemical properties mimic naturally-occurring materials is quite difficult, as pointed out by K. Murray and P. W. Linder, *J. Soil Sci.* 1983, 34, 511–523. Nevertheless, there have been several notable advances in this area. Broadly speaking, three general strategies have evolved. All depend upon starting with well-defined molecules of molecular weight on the order of hydroxybenzoic acid, and then causing the molecules to polymerize upon themselves to form larger molecules. The methods differ in the causation factor, which can be microbial, chemical, or enzymatic.

Humic acids of microbial origin have been described and discussed by M. Robert-Gero, C. Hardisson, L. Le Borgne, and G. Pignaud, *Ann. Inst. Pasteur (Paris)* 1966, 111(6), 750–767; and by M. Robert-Gero, C. Hardisson, L. Le Borgne, and G. Vidal, *Ann. Inst. Pasteur (Paris)* 1967, 113(6), 903–909.

The chemical synthesis of humic acids has been pioneered by R. Klocking, B. Helbig, and associates: R. Klocking, B. Helbig, and P. Drabke, *Pharmazie* 1977, 32, 297; R. Klocking, B. Helbig, K. D. Thiel, T. Blumohr, P. Wutzler, M. Sprossig, and F. Schiller, *Pharmazie* 1979, 34(5–6), 293–294; R. Mentel, B. Helbig, R. Klocking, L. Dohner and M. Sprossig, *Biomed. Biochim. Acta* 1983, 42(10), 1353–1356; H. P. Klocking, R. Klocking, and B. Helbig, *Farmakol. Toksikol.* 1984, 47(1), 93–95; K. D. Thiel, P. Wutzler, B. Helbig, R. Klocking, M. Sprossig, and H. Schweizer, *Pharmazie* 1984, 39(11), 781–782; J. Hils, A. May, M. Sperber, R. Klocking, B. Helbig, and M. Sprossig, *Biomed. Biochim. Acta* 1986, 45(9), 1173–1179; B. Helbig, A. Sauerbrei, R. Klocking, P. Wutzler, N. Wicht, U. Wiedemann, and G. Herrmann, *J. Med. Virol.* 1987, 23(3), 303–309; K. I. Hanninen, R. Klocking, and B. Helbig, *Sci. Total Environ.* 1987, 62, 201–210; R. Klocking and B. Helbig, in *Humic Substances in the Aquatic and Terrestrial Environment*; New York: Springer-Verlag, 1989; 407–412; C. Schewe, R. Klocking, B. Helbig, and T. Schewe, *Biomed. Biochim. Acta* 1991, 50(3), 299–305; D. Schols, P. Wutzler, R. Klocking, B. Helbig, and E. De Clercq, *J. Acquir. Immune Defic. Syndr.* 1991, 4(7), 677–685. Typically, 10 millimoles of the starting small-molecule phenolic compound is dissolved in distilled water, the pH is adjusted to 8.5 with aqueous sodium hydroxide (NaOH), and then 2–5 millimoles of sodium periodate ($NaIO_4$) is added. The solution is warmed at 50° C. for 30 minutes, and is then allowed to stand overnight. The resultant humic acid-like polymeric products are isolated by precipitation with lead(II) nitrate [$Pb(NO_3)_2$]. The precipitated polymers are redissolved in aqueous sodium hydroxide (pH 8.5) and heated with 8-hydroxyquinoline for 30 minutes at 100° C. The precipitate formed is lead(II) chelate, which is removed by filtration. Residual 8-hydroxyquinoline is extracted with chloroform, and the desired polymeric material is then precipitated from the aqueous solution by the addition of various combinations of acetic acid, ethyl acetate, and ethanol. Starting compounds that have been used for the synthesis of humic-like materials include 4-[bis(p-hydroxyphenyl)methylene]-2,5-cyclohexadie-1-one (aurin), 4-[bis(3-carboxy-4-hydroxyphenyl)methylene]-2-carboxy-2,5-cyclohexadien-1-one (aurintricarboxylic acid), 3-(3,4-dihydroxyphenyl)propenoic acid (caffeic acid), 1,2-dihydroxybenzene (catechol), 1,3,4,5-tetrahydroxycyclohexanecarboxylic acid 3-(3,4-dihydroxyphenyl)propenoate (chlorogenic acid), 3,4-dihydroxyphenylacetic acid (homoprotocatechuic acid), 1-(3,4-dihydroxyphenyl)-2-(N-methylamino)ethanol (epinephrine), 3-(4-hydroxy-3-methoxyphenyl)-2-propenoic acid (ferulic acid), 3,4–5-trihydroxybenzoic acid (gallic acid), 2,5-dihydroxybenzoic acid (gentisic acid), 2,5-dihydroxyphenylacetic acid (homogentisic acid), 3-(3,4-dihydroxyphenyl)propionic acid (hydrocaffeic acid), 1,4-dihydroxybenzene (hydroquinone), 2,3-dihydroxytoluene (3-methylcatechol), 3,4-dihydroxytoluene (4-methylcatechol), 2,5-dihydroxytoluene (2-methylhydroquinone), 4,4'-(2,3-dimethyltetramethylene)-di-( 1,2-dihydroxybenzene) (nordihydroguaiaretic acid), 1-(3,4-dihydroxyphenyl)-2-aminoethanol (norepinephrine), 3,4-dihydroxybenzoic acid (protocatechuic acid), 1,2,3-trihydroxybenzene (pyrogallol), 1,3-dihydroxybenzene (resorcinol), and 4-hydroxy-3-methoxybenzoic acid (vanillic acid). Other notable efforts on the chemical synthesis of humic-like substances include the studies by De Clercq and colleagues on aurintricarboxylic acid, its derivatives, and related compounds: M. Cushman, P. Wang, S. H. Chang, C. Wild, E. De Clercq, D. Schols, M. E. Goldman, and J. A. Bowen, *J. Med Chem.* 1991, 34(1), 329–337; M. Cushman, S. Kanamathareddy, E. De Clercq, D. Schols, M. E. Goldman, and J. A. Bowen, *J. Med Chem.* 1991, 34(1), 337–342. Related efforts have also been reported by M. Robert-Gero, C. Hardisson, L. Le Borgne, and G. Vidal, *Ann. Inst. Pasteur (Paris)* 1967, 113(6), 903–909; M. Jakubiec, E. Miszczak, and J. Szczerkowska, *Acta Microbiol. Pol. [B]* 1971, 3(1), 63–66; R. Ansorg and W. Rochus, *Arzneimittelforschung* 1978, 28(12), 2195–2198; J. Pommery, M. Imbenotte, A. F. Urien, D. Marzin, and F. Erb, *Mutat. Res.* 1989, 223(2), 183–189; F. J. Lu and Y. S. Lee, *Sci. Total Environ.* 1992, 114, 135–139; K. Wiegleb, N. Lange, and M. Kuhnert, *DTW Dtsch. Tierarztl. Wochenschr.* 1993, 100(10), 412–416; H. L. Yang, F. J. Lu, S. L. Wung, and H. C. Chiu, *Thromb. Haemost.* 1994, 71(3), 325–330; W. Seffner, F. Schiller, R. Heinze, and R. Breng, *Exp. Toxicol. Pathol.* 1995, 47(1), 63–70; and J. Schneider, R. Weis, C. Manner, B. Kary, A. Werner, B. J. Seubert, and U. N. Riede, *Virology* 1996, 218(2), 389–395.

The enzymatic catalytic synthesis of humic acids dates to about 1961 with the work by R. E. Hampton and R. W. Fulton, *Virology* 1961, 13, 44–52 (see also R. E. Hampton, *Phytophathology* 1970, 60, 1677–1681), who found that enzymatically oxidized phenols inactivate phytopathogenic (i.e., plant-related) viruses. Typically o-diphenol oxidase has been employed for the enzymatic synthesis of humic-like materials: anon. *Zentralbl. Bakteriol. [Orig. A]* 1976, 234 (2), 159–169; R. Klocking, B. Helbig, and P. Drabke, *Pharmazie* 1977, 32(5), 297; K. D. Thiel, B. Helbig, R. Klocking, P. Wutzler, M. Sprossig, and H. Schweizer, *Pharmazie* 1981, 36(1), 50–53; K. D. Thiel, B. Helbig, M. Sprossig, R. Klocking, and P. Wutzler, *Acta Virol.* 1983, 27(3), 200–208; K. D. Thiel, P. Wutzler, B. Helbig, R. Klocking, M. Sprossig, and H. Schweizer, *Pharmazie* 1984, 39(11), 781–782; and G. Sydow, V. Wunderlich, R. Klocking, and B. Helbig, *Pharmazie* 1986, 41 (12), 865–868.

A direct comparison of humic acids synthesized enzymatically and nonenzymatically from caffeic and hydrocaffeic acids has shown that the two synthetic routes produce materials that differ somewhat in their efficacy for the suppression of herpes (hominis) types 1 and 2 viruses: K. D. Thiel, P. Wutzler, B. Helbig, R. Klocking, M. Sprossig, and H. Schweizer, *Pharmazie* 1984, 39(11), 781–782.

German patent DE 3830333 C1 (Mar. 15, 1990) issued to Wagner discloses a pharmaceutical composition comprised in part of humic acid for the topical treatment of herpes virus-induced vesicular rash. The method of preparation of the humic acid utilized is not disclosed.

U.S. Pat. No. 4,999,202 (Mar. 12, 1991) issued to Cronje, et al disloses a composition that has bactericidal or bacteriostatic properties, and which comprises oxidized coal-derived humic acid or a salt or derivative thereof as the active ingredient in a suitable carrier. The active ingredient is preferably an alkali metal salt of coal-derived humic acid and the carrier is preferably water. The method of preparation involves recovery of the humic acid by precipitation, after acidification with an acid such as hydrochloric acid to a pH value of 2.

European patent application 0537430A1 (Apr. 21, 1993) from Riede, et al. discloses the use of natural or synthetic, modified or unmodified ammonium or alkali metal humates against viruses, especially against retroviruses such as HIV. Riede et al. disclose humates that have insignificant toxicity and are neither mutagens nor teratogens. Riede, et al. also disclose a specific synthetic preparation of said humates that requires as long as 10–15 days to complete the oxidation of the starting material during which time the reaction temperature is maintained below 40° C. The solution is acidified to pH 4–5 following the synthesis, following which known methods of purification, such as preparative chromatography, ultrafiltration, centrifugation, or electrodialysis, are employed. No inorganic salts other than the oxidant or the starting material are employed during or after the synthesis.

World patent application 95/08335 (published Mar. 30, 1995) from Zanetti, which is equivalent to U.S. application 08/310,675 (filed Sep. 22, 1994) discloses a method of inhibiting human immunodeficiency virus infection that comprises contacting leukocytes, peripheral blood mononuclear cells, and lymphocytes of an individual infected with said virus with an anti- immunodeficiency virus amount of a natural, commercially available preparation of humic acid. Synthetic humic acid preparations are also disclosed. The synthetic procedure disclosed employs no inorganic salts other than sodium periodate for the oxidation of the starting material. The synthetic procedure employs acidification of the product of the synthesis with 6 M HCl to a pH of less than 1. This solution is allowed to stand overnight. A precipitate of the synthetic product forms which is washed several times with 1M HCl. The final step involves freeze drying the precipitate.

Phenolic polymers such as humic acid, when exposed to hydrochloric acid under the above conditions as well as the conditions in Cronje '202, may be chlorinated. That is, one or more chlorine atoms will possibly be added to the aromatic rings of the phenolic polymers: R. B. Wagner and H. D. Zook, *Synthetic Organic Chemistry*, New York: J. Wiley & Sons, March 1963, 88–147. Other changes such as selective 0-demethylation of humic acid products may also occur in the presence of hydrochloric acid: M. Fieser and L. F. Fieser, *Reagents For Organic Synthesis*, New York, Wiley-Interscience, Vol. 4, 1974, 250. It has been reported that aqueous chlorination of humic acids results in the formation of compounds with direct-acting mutagenic activity in the Ames/Salmonella plate assay. Nonchlorinated humic acids are not mutagenic: J. R. Meier, R. D. Lingg, R. J. Bull, *Mutat. Res.,* 1983, 118(1–2), 25–41. It has also been reported that freeze-dried, chlorinated humic acid contains nonvolatile, direct-acting mutagenic and/or alkylating agents: S. C. Agarwal, J. Neton, *Sci. Total Environ.,* 1989, 79(1), 69–83. A subchronic 90-day toxicology study has been conducted with chlorinated and nonchlorinated humic acids using male Sprague-Dawley rats. Increased incidence and severity of hematuria was found in the 1.0-g/l chlorinated humic acid group: L. W. Condie, R. D. Laurie, J. P. Bercz, *J. Toxicol. Environ. Health,* 1985, 15(2), 305–14. Thus, synthetic methods for the production of humic acids that can possibly produce chlorinated humic acids are to be avoided.

Another area of related art relevant to this invention is comprised of blood product compositions and methods for treating blood products to reduce viral and microbial activity. A variety of human blood products including blood platelets exist to meet critical medical therapeutic needs. Viral safety depends upon donor selection and screening. It has proven to be impossible to date to screen blood products adequately to provide complete assurance that there is no viral contamination. These blood products may be inadvertently contaminated with viruses such as HIV-human immunodeficiency virus, hepatitus virus, including hepatitus A, B, and C and other viruses. A solvent/detergent (SD) technique exists for treating blood products including blood platelets, but this technique is primarily limited to lipid enveloped viruses and is known to be ineffective for nonenveloped viruses such as hepatitus A, parvovirus B19 and picornaviruses: P. M. Mannucci, et al., *Ann. Intern. Med.,* 1994, 120(1),1–7; and L. Gurtler, *Infusionsther. Transfusionsmed.,* 1994, 21(Suppl 1), 77–9. Additionally, it is necessary to separate the detergents in the SD method from the blood product utilizing extraction with soybean or castor oil and chromatography on insolubilized C18 resin: B. Horowitz et al., *Blood,* 1992, 79(3), 826–31; and Y. Piquet et al., *Vox Sang.,* 1992, 63(4), 251–6.

A pasteurization process has been developed for treating blood products. This involves heat treatment of a stabilized aqueous protein solution at 60° C. for 10 hours. However, residual infectious hepatitus A virus has been found even after 10 hour heat treatment of the stabilized preparation: J. Hilfenhaus and T. Nowak, *Vox Sang,* 1994, 67(Suppl 1), 62–6. Neither the solvent/detergent (S/D) process nor the pasteurization process alone are adequate to inactivate viruses that are strongly resistant to heat and organic solvents. In this context, human parvovirus B19 and hepatitus A virus are of particular concern: H. Schwinn et al., *Arznneimittelforschung,* 1994, 44(2), 188–91.

A final super heat treatment (100° C. for 30 min) has been developed as an additional virus inactivation step to improve the safety of plasma derived factor VIII (FVIII) concentrate already treated with the solvent/detergent (S/D) method during the manufacturing process. The efficiency of the super heat treatment was demonstrated in inactivating two nonlipid enveloped viruses (Hepatitis A virus and Poliovirus 1). However, the loss of FVIII procoagulant activity during the super heat treatment was about 15%, estimated both by clotting and chromogenic assays: S. Arrighi et al., *Thromb. Haemost.,* 1995, 74(3), 863–73.

A method for treating human blood products employing short wavelength ultraviolet light (UVC) irradiation for virus inactivation and enhancement of its compatibility with proteins by quenchers of reactive oxygen species has been developed. However, blood protein recovery was typically only around 75%: S. Chin et al., *Blood,* 1995, 86(11), 4331–6. Ultraviolet irradiation methods have additionally been reported not to be applicable to cellular blood products: C. M. Allen, *Photochem. Photobiol.,* 1995, 62(1), 184–9.

In summary, there remains a need for a safe, efficacious and simple method for treating all human blood products to reduce or eliminate lipid enveloped and nonenveloped virus activity without loss of blood product or blood product activity.

The diversity of physicochemical characteristics as well as wide variation in the biological activity and toxicity of humics extracted or otherwise derived from natural soils has been well documented. This diversity and variation is due to variations in factors such as the source of the soil, the method(s) of extraction and/or isolation, and the technique(s) employed to treat the extract once it has been separated and isolated from crude soil. The consequence of irreproducibility of the properties of substances extracted from natural soil is that the commercial value of such materials is minimized. In addition, they are rendered unsuitable as medicaments. Also, while a number of laboratory-scale processes have already been described that address various aspects of the isolation, synthesis, and/or preparation of humic substances or similar materials, there are no reports of preparing and isolating such purely synthetic humic acids or similar materials by methods that are suitable for scaleup directly to industrial levels, that provide economically acceptable yields, and that optimize the preparation procedures from the standpoint of medicament safety and efficacy. All of the known synthetic methods utilize potentially toxic precipitation methods ( lead(II) nitrate precipitation ) followed by complex isolation procedures, potentially mutagenic compound-producing hydrochloric acid precipitation or lengthy synthetic steps as long as 10 days. The solution is to devise simple synthetic procedures that yield inexpensive, safe materials whose physicochemical attributes are reproducible, and that at least simulate those of typical commercially-available soil extracts. This invention is directed to this solution and to compositions and methods employing synthetic materials prepared according to the process of the invention.

SUMMARY OF THE INVENTION

One aspect of the invention is a process for preparing synthetic phenolic polymeric materials whose physicochemical properties and attributes are reproducible, and which simulate the physicochemical properties and attributes of typical commercially-available natural humic acids and other soil extracts. This process comprises the steps of:

a) dissolving one or more starting organic compounds selected from the group consisting of the compounds listed in Table 1 and Table 2 in an aqueous solution comprising distilled water or sodium hydroxide;

b) adjusting the pH of the aqueous solution resulting from step a) to between 8 and 11 if necessary;

c) adding an alkaline periodate salt or alkaline-earth periodate salt to the aqueous solution resulting from step b);

d) maintaining the temperature of the solution resulting from step c) between 35 and 80° C. for a period of 30 minutes to 100 hours;

e) adding one or more compounds or salts selected from the group consisting of boric acid, borate salts, alkaline earth salts, transition metal salts, alkaline sulfides, alkaline earth sulfides or transition metal sulfides to the aqueous solution resulting from step d);

f) allowing the aqueous solution resulting from step e) to stand with or without stirring at room temperature between 2 and 48 hours;

g) removing molecules from the solution resulting from step f) below about 500 to about 10,000 daltons;

h) concentrating the solution resulting from step g); and i) removing the water from the solution resulting from step h) if necessary.

In one embodiment of the process, the pH of the aqueous solution resulting from step a) is adjusted to between 8 and 11 by adding aqueous ammonium hydroxide, or other aqueous alkaline oxide or hydroxide, or aqueous alkaline-earth oxide or hydroxide, or aqueous transition-metal oxide or hydroxide, or hydrochloric acid or other inorganic acid. In another embodiment of the process, the alkaline or alkaline-earth sulfides are added to the solution resulting from step b). Alternatively, the alkaline or alkaline-earth sulfides are added to the solution resulting from step c). In another embodiment of the process, transition-metal sulfides are added to the solution resulting from step b). Alternatively, transition-metal sulfides are added to the solution resulting from step c). In another embodiment of the process, any precipitate formed from the solution resulting from step f) is removed by centrifugation. In another embodiment of the process, step g) is accomplished by dialyzing the solution resulting from step f) with a flow-through apparatus consisting of a sandwich-type membrane of molecular-weight cutoff of 500–10,000 daltons until the conductivity of the retentate solution has dropped to 200 microsiemens or less. In a further embodiment of the process following dialysis in step g), the solution resulting from step g) is concentrated in step h) by utilizing a flow-through dialysis apparatus that produces a retentate solution such that the volume of the dialysis apparatus retentate solution is allowed to drop. In another embodiment of the process, the solution resulting from step g) is passed through a filter of pore size between 0.2 and 0.4 micron to produce a sterile solution. In another embodiment of the process, the solution resulting from step g) is autoclaved between 100 and 150° C. for 5 to 60 minutes to produce a sterile solution. In another embodiment of the process, the solution resulting from step h) is passed through a filter of pore size between 0.2 and 0.4 micron to produce a sterile solution. In another embodiment of the process, the solution resulting from step h) is autoclaved between 100 and 150° C. for 5 to 60 minutes to produce a sterile solution. In another embodiment of the process, mannose or other static electricity reduction material is added to the solution resulting from step h) prior to removing the water from said solution in step i). In another embodiment of the process, step i) is accomplished by spray-drying or thermally-induced evaporation or vacuum or freeze-drying. In another embodiment of the process, the dried powder from step i) is autoclaved between 100 and 150° C. for 5 to 60 minutes to produce a sterile powder. In another embodiment of the process, tubular, capillary, coiled-spiral, or plane dialysis membranes are used in step g) for removing molecules from the solution resulting from step f). In a further embodiment of the process employing tubular, capillary, coiled spiral, or plane dialysis membranes in step g), the solution resulting from step g) is passed through a filter of pore size between 0.2 and 0.4 micron to produce a sterile solution. Alternatively, the solution resulting from step g) which employed tubular, capillary, coiled-spiral, or plane dialysis emembranes is autoclaved between 100 and 150° C. for 5 to 60 minutes to produce a sterile solution. In a further embodiment of the process employing tubular, capillary, coiled-spiral, or plane dialysis membranes in step g), the solution resulting from step g) is concentrated in step h) by utilizing a flow-through dialysis apparatus that produces a retentate solution such that the volume of the dialysis apparatus retentate solution is allowed to drop. In another embodiment of the process of the invention, the solution resulting from step g) is further dialyzed with a flow-through apparatus consisting of a sandwich-type membrane of molecular-weight cutoff of 30,000–100,000 daltons to produce an aqueous filtrate solution containing synthetic phenolic polymeric materials of lower molecular weight between 500 and 10,000 daltons and upper molecular weight between 30,000 and 100,000 daltons. In a further embodiment of the prior process employing further dialysis, tubular, capillary, coiled spiral, or plane dialysis membranes are used for said further dialysis. In a further embodiment of the prior process employing tubular, capillary, coiled spiral, or plane dialysis membranes in step g), the solution resulting from step g) is passed through a filter of pore size between 0.2 and 0.4 micron to produce a sterile solution. Alternatively, the solution resulting from step g) which employed tubular, capillary, coiled-spiral, or plane dialysis membranes is autoclaved between 100 and 150° C. for 5 to 60 minutes to produce a sterile solution. In a further embodiment of the previous process employing tubular, capillary, coiled-spiral, or plane dialysis membranes in step g), the solution resulting from step g) is concentrated in step h) by utilizing a flow-through dialysis apparatus that produces a retentate solution such that the volume of the dialysis apparatus retentate solution is allowed to drop.

In another aspect of the invention, a blood product composition is provided comprising an anti-viral amount of a synthetic phenolic polymeric material produced by the process of the invention combined with a blood product. In one embodiment of the blood product composition, said blood product is whole human blood. In another embodiment of the blood product composition, said blood product is human blood platelets. In another embodiment of the human blood platelet blood product composition, the anti-viral amount is an amount sufficient to reduce human immunodeficiency virus (HIV) activity. In yet another embodiment of the human blood platelet blood product composition, the anti-viral amount is an amount sufficient to reduce non-enveloped virus activity. Preferably, the non-enveloped virus is parvovirus or cytomegalovirus. In another embodiment of the blood product composition, said blood product is human blood serum. In another embodiment of the blood product composition, said blood product is a human blood protein. Preferably, said human blood protein is human serum albumin or human serum gamma-globulin. In another embodiment of the blood product composition, said blood product is a human haemophilia factor. Preferably, the human haemophilia factor is factor VIII or factor IX. In a further embodiment of the blood product composition wherein said blood product is a human haemophilia factor, the anti-viral amount is sufficient to reduce human immunodeficiency virus (HIV) activity. Alternatively, the anti-viral amount is sufficient to reduce non-enveloped virus activity. Preferably, the non-enveloped virus is parvovirus or cytomegalovirus.

In yet another aspect of the invention, there is provided a method of reducing the amount of virus in a blood product by contacting said blood product with an anti-viral amount of a synthetic phenolic polymeric material produced by the process of the invention. In one embodiment of the method of reducing the amount of virus in a blood product, said contacting consists of sterily breaking a seal in a connecting path between two separate chambers, one of which contains said blood product in a sterile form and the other of which contains said anti-viral amount of said synthetic phenolic polymeric material in sterile form. In another embodiment of the aforementioned method, said contacting consists of injecting a sterile solution containing said anti-viral amount into said blood product. In another embodiment of the method above, said virus is preferably Human Immunodeficiency Virus (HIV). In another preferred embodiment of the above method, said virus is Hepatitis A virus, Hepatitis B virus, Hepatitis C virus, parvovirus, or cytomegalovirus. In another embodiment of the above method, one or more additional blood treatment methods for reducing viral activity are employed. Preferably, the additional blood treatment method is the solvent/detergent (SD) method.

In a further aspect of the invention, there is provided a composition for treating or preventing human or animal diseases caused by a virus comprising an anti-viral amount of a synthetic phenolic polymeric material produced by the process of the invention and at least one physiologically acceptable carrier or excipient. Preferably, the virus is Human Immunodefiency Virus (HIV), Herpes Simplex Virus Type I or Type II, or is a picornavirus. Preferably, the physiologically acceptable carrier or excipient is an injectable solution excipient, a topical formulation excipient, an ingestable excipient, a nasal spray excipient, a metered-dose inhaler excipient, vaginal or anal suppository excipient, or an excipient suitable for disinfection or preservation of a medical device.

Still another aspect of the invention provides a composition for treating or preventing human or animal microbial-induced diseases comprising an antimicrobial amount of a synthetic phenolic polymeric material produced by the process of the invention and at least one physiologically acceptable excipient. Preferably, the physiologically acceptable carrier or excipient is an injectable solution excipient, a topical formulation excipient, an ingestable excipient, a nasal spray excipient, a metered-dose inhaler excipient, vaginal or anal suppository excipient, or an excipient suitable for disinfection or preservation of a medical device. Preferably, the medical device is a contact lens, intraocular lens, dental prosthesis, implantable medical device such as a heart valve or a medical instrument which contacts the body such as an endoscope or catheter.

DETAILED DESCRIPTION OF THE PREFERRED EMBODIMENT

Figure 1:
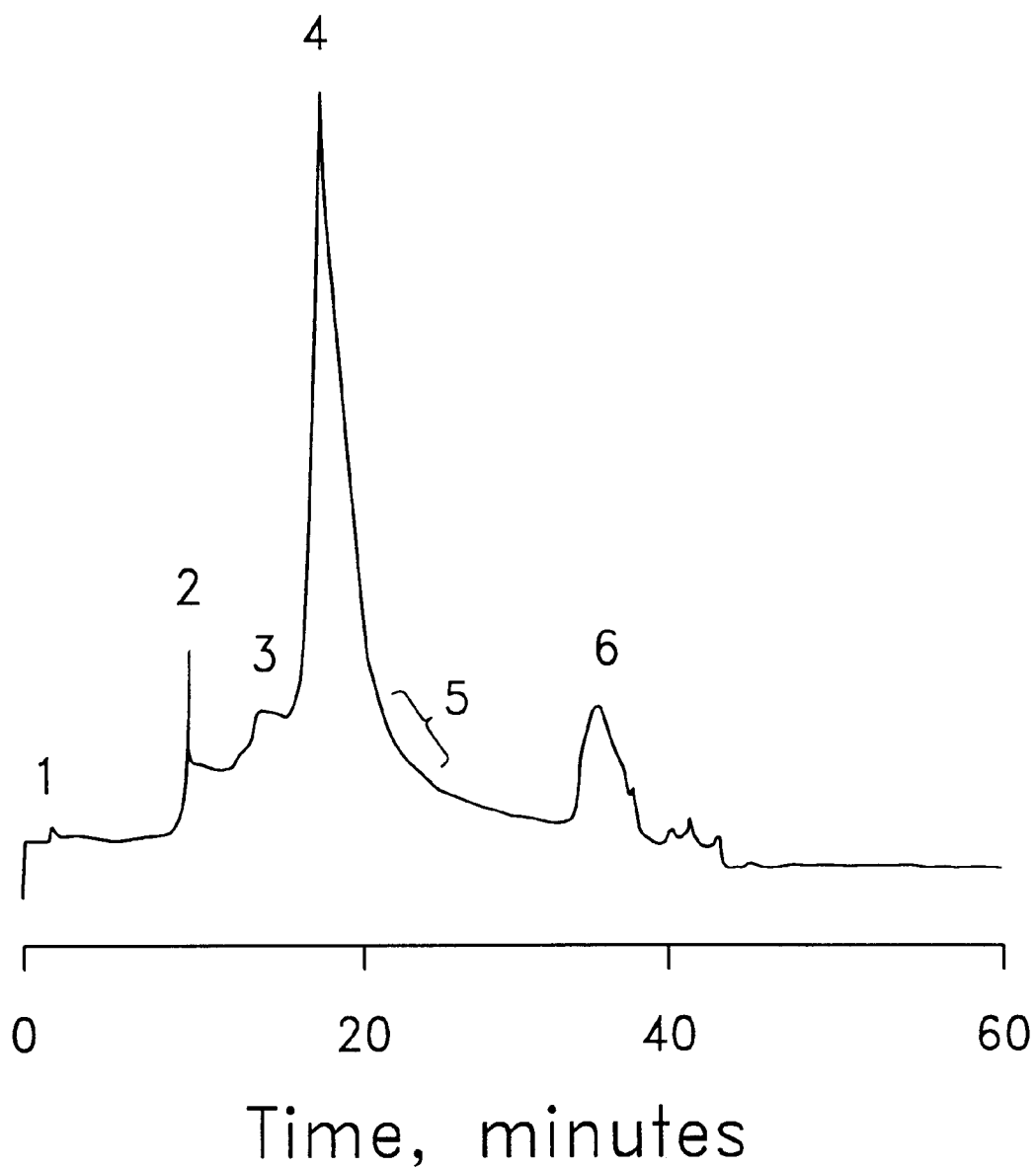
FIG. 1 shows the high-performance liquid chromatography (HPLC) trace obtained for the synthetic humic acid product obtained from 2,5-dihydroxyphenylacetic acid (homogentisic acid), as described in Examples 10 and 11.

An object of the present invention is to provide new and improved combinations of chemical processes for the preparation of synthetic phenolic polymeric materials, also known as synthetic humic acids, whose physicochemical properties and attributes are reproducible, and which simulate those of typical commercially-available natural humic acids and other soil extracts, which contain no ionic salts or other compounds of molecular weight less than 500 daltons, which have a minimum molecular weight of 500 daltons, and which processes shall be suitable for scaleup directly to industrial levels that provide economically acceptable yields.

Still another object of the present invention is to provide human or animal blood product compositions comprising an anti-viral amount of a synthetic humic acid prepared according to the above processes.

Still another object of the present invention is to provide methods for reducing or eliminating the amount of virus in human or animal blood products by contacting said blood products with an anti-viral amount of a synthetic humic acid prepared according to the above processes.

Still another object of the present invention is to provide compositions for treating or preventing human or animal viral diseases comprising an anti-viral amount of a synthetic humic acid prepared according to the above processes.

Still another object of the present invention is to provide compositions for treating or preventing human or animal microbial diseases comprising an anti-microbial amount of a synthetic humic acid prepared according to the above processes.

According to the present invention the starting compounds used in the chemical processes employed for production of synthetic humic acids are known materials that are readily available commercially.

Generally speaking, the chemical processes for the preparation of synthetic humic acids of the invention are characterized by the following steps:

A. Dissolving the starting organic compound or mixture of organic compounds in an aqueous solution comprising distilled water or sodium hydroxide.

B. Adjusting the pH of the aqueous solution resulting from step A) to between 8 and 11 if necessary.

C. Adding an alkaline periodate salt or alkaline-earth periodate salt to the aqueous solution resulting from step B).

D. Maintaining the temperature of the solution resulting from step C) between 35 and 80° C. for a period of 30 minutes to 100 hours.

E. Adding one or more compounds or salts selected from the group consisting of boric acid, borate salts, alkaline earth salts, transition metal salts, alkaline sulfides, alkaline earth sulfides or transition metal sulfides to the aqueous solution resulting from step D);

F. Allowing the aqueous solution resulting from step E) to stand with or without stirring at room temperature between 2 and 48 hours.

G. Removing molecules from the solution resulting from step F) below about 500 to about 10,000 daltons.

H. Concentrating the solution resulting from step G).

I. Removing the water from the solution resulting from step H) if necessary.

The starting organic compound in step A) above can be one, or more than one in combination, of different compounds taken from the group consisting of starting organic compounds illustrated in Tables 1 and 2. Starting organic compounds illustrated in Table 1 are comprised of a single benzene ring with six substituents R1–R6, wherein R1–R6 can be any one of the indicated atom or functional groups, as long as at least one of R1–R6 is a hydroxy (—OH) functional group. Preferably, at least one of R1–R6 is a hydroxy (—OH) functional group and at least one of the remaining substituents R1–R6 contains a carboxylic acid functional group. More preferably, two of R1–R6 are hydroxy (—OH) functional groups and one of the remaining substituents R1–R6 contains a carboxylic acid functional group. Homogentisic acid, which is 2,5-dihydroxyphenylacetic acid, is a particularly preferred starting organic compound.

Various initial concentrations of starting organic compounds in distilled water can be employed and no lower or upper limits are uniformly required. A low concentration solution of sodium hydroxide, such as 0.1 Normal, may also be employed as a diluent for the starting organic compound. The appropriate initial concentration of the starting organic compound or compounds is determined by the

TABLE 1

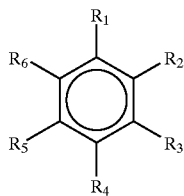

$R_1, R_2, R_3, R_4, R_5, R_6 =$

—H
—CH$_3$
—CH$_2$CH$_3$
—(CH$_2$)$_2$CH$_3$
—CH(CH$_3$)$_2$
—OH
—OCH$_3$
—CHO
—CO$_2$H
—CO$_2$CH$_3$
—CH$_2$OH
—CH$_2$OCH$_3$
—CH$_2$CHO

TABLE 1-continued

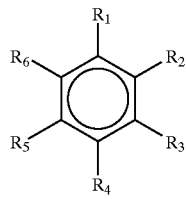

$R_1, R_2, R_3, R_4, R_5, R_6 =$

—CH$_2$CO$_2$H
—CH$_2$CO$_2$CH$_3$
—(CH$_2$)$_2$OH
—(CH$_2$)$_2$OCH$_3$
—(CH$_2$)$_2$CHO
—(CH$_2$)$_2$CO$_2$H
—(CH$_2$)$_2$CO$_2$CH$_3$
—CH(CH$_3$)OH
—CH(CH$_3$)OCH$_3$
—CH(CH$_3$)CHO
—CH(CH$_3$)CO$_2$H
—CH(CH$_3$)CO$_2$CH$_3$
—CH(CH$_3$)CH$_2$OH
—CH(CH$_3$)CH$_2$OCH$_3$
—CH(CH$_3$)CH$_2$CHO
—CH(CH$_3$)CH$_2$CO$_2$H
—CH(CH$_3$)CH$_2$CO$_2$CH$_3$
—CH(OH)$_2$
—CH(OH)OCH$_3$
—CH(OH)CHO
—CH(OH)CO$_2$H
—CH(OH)CO$_2$CH$_3$
—CH(OCH$_3$)OH
—CH(OCH$_3$)$_2$
—CH(OCH$_3$)CHO
—CH(OCH$_3$)CO$_2$H
—CH(OCH$_3$)CO$_2$CH$_3$
—CH(OH)CH$_2$OH
—CH(OH)CH$_2$OCH$_3$
—CH(OH)CH$_2$CHO
—CH(OH)CH$_2$CO$_2$H
—CH(OH)CH$_2$CO$_2$CH$_3$
—CH(OCH$_3$)CH$_2$OH
—CH(OCH$_3$)CH$_2$OCH$_3$
—CH(OCH$_3$)CH$_2$CHO
—CH(OCH$_3$)CH$_2$CO$_2$H
—CH(OCH$_3$)CH$_2$CO$_2$CH$_3$
—(CH$_2$)$_3$OH
—(CH$_2$)$_3$OCH$_3$
—(CH$_2$)$_3$CHO
—(CH$_2$)$_3$CO$_2$H
—(CH$_2$)$_3$CO$_2$CH$_3$
—CHCHOH (cis or trans)
—CHCHOCH$_3$ (cis or trans)
—CHCHCHO (cis or trans)
—CHCHCO$_2$H (cis or trans)
—CHCHCO$_2$CH$_3$ (cis or trans)
—CH$_2$CHCHOH (cis or trans)
—CH$_2$CHCHOCH$_3$ (cis or trans)
—CH$_2$CHCHCHO (cis or trans)
—CH$_2$CHCHCO$_2$H (cis or trans)
—CH$_2$CHCHCO$_2$CH$_3$ (cis or trans)

TABLE 2

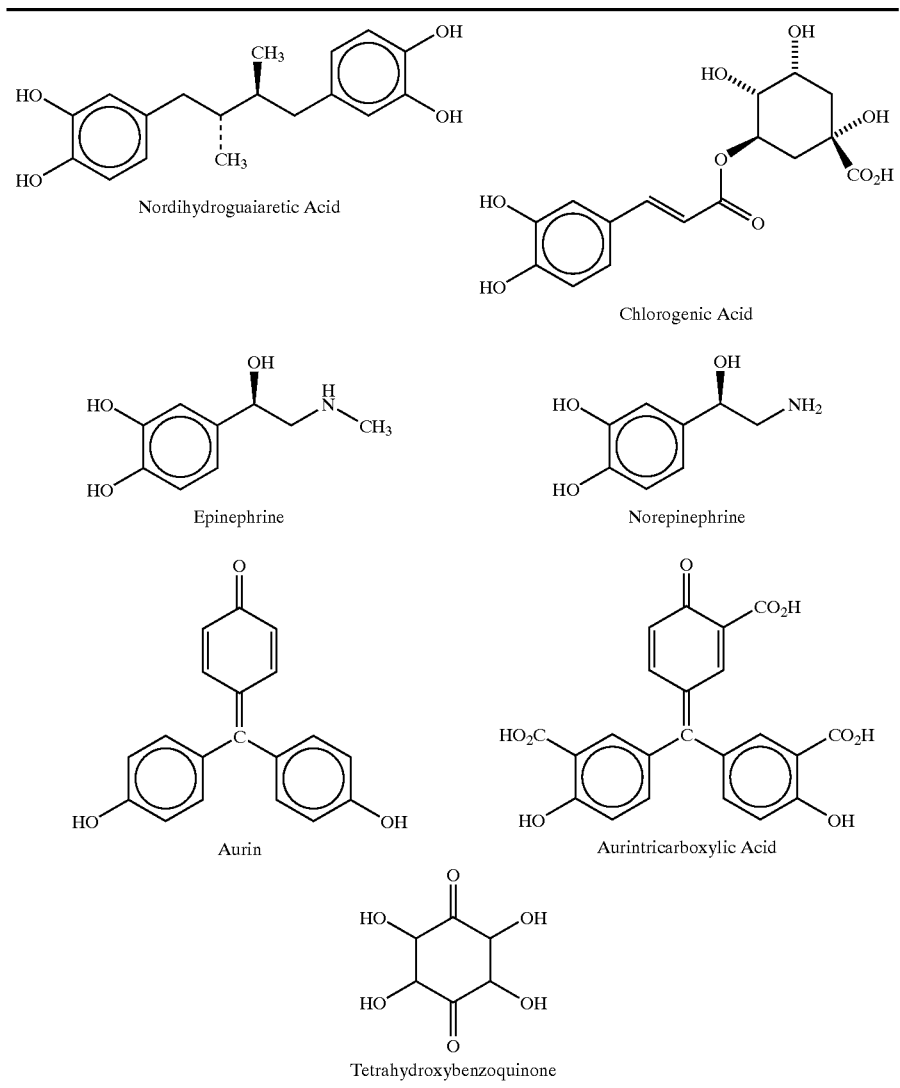

synthesis yield requirements and inherent requirements, such as the upper limit of aqueous solubility of the starting organic compound or compounds. Conventional methods are employed to determine the appropriate initial concentration of the starting organic compound or compounds.

The pH of the aqueous solution containing the starting organic compound or compounds can be adjusted in step B) to between 8 and 11 by adding aqueous ammonium hydroxide, or other aqueous alkaline oxide or hydroxide, or aqueous alkaline earth oxide or hydroxide, or aqueous transition metal oxide or hydroxide. Additonally, if the initial aqueous solution contains a low concentration of base, such as 0.1 Normal sodium hydroxide and the initial solution pH is too high, an acid such as hydrochloric acid may be employed to adjust the pH to the desired value. Other inorganic acids may also be employed for pH adjustment. Note that if hydrochloric acid is employed to adjust the pH downwards from an initial high value, care should be taken to avoid letting the pH go below 8. Acidic conditions below pH 7 should be avoided in the presence of hydrochloric acid to eliminate the possibility of formation of mutagenic chlorinated humic acid materials.

An alkaline periodate salt or alkaline earth periodate salt may be employed as an oxidant or polymerization initiator of the starting organic compound in step C). Sodium periodate is particularly preferred. The concentration of the alkaline periodate salt or alkaline earth periodate salt is generally between 10% and 100% of the starting organic compound or compounds on a molar basis. Thus, if 10 millimoles of starting organic compound is employed, 1 to 10 millimoles of alkaline periodate salt may be employed. Preferably, a molar concentration of periodate which is 10–50% of the molar concentration of the starting organic compound or compounds is employed. Most preferably, a molar concentration of periodate which is 25–35% of the molar concentration of the starting organic compound or compounds is employed. The exact concentration to be used can be determined by conventional synthetic yield optimization techniques.

Alkaline or alkaline earth sulfides or transition metal sulfides can be optionally added to the initial aqueous solution containing the starting organic compound or compounds following the pH adjustment step B) and immediately before, at the same time or following the addition of the periodate in step C). Sulfides contribute to the phenolic polymeric structure, the stability of the structure and its biological activity. Sodium sulfide nonahydrate is a particularly preferred sulfide. The concentration of the sulfide is generally between 1% and 20% of the starting organic compound or compounds on a molar basis. Thus, if 10 millimoles of starting organic compound is employed, 0.1 to 2 millimoles of sulfide may be employed. Preferably, a molar concentration of sulfide which is 5–15% of the molar concentration of the starting organic compound or compounds is employed. Most preferably, a molar concentration of sulfide which is 8% to 12% of the molar concentration of the starting organic compound or compounds is employed. The exact concentration of sulfide to be used can be determined by conventional synthetic yield optimization techniques.

The pH-adjusted aqueous solution containing the starting organic compound, periodate and optional sulfide is placed in a water-bath or other thermostat heating device at between 35° C. and 80° C. for a period of 30 minutes to 100 hours in step D). Alternatively, the aqueous solution itself may be thermostated between 35° C. and 80° C. for a period of 30 minutes to 100 hours. A preferred temperature and time is 50° C. for 30 minutes.

Following this period, salts are added to the solution resulting from step D) alone or in combination in step E). Salts containing boron, calcium and other alkaline earths, iron and other transition metals are preferred. Such salts additionally contribute to the phenolic polymeric structure, its stability and biological activity. Boric acid or boron-containing-borate salts such as sodium borate are particularly preferred, as are alkaline earth salts, such as calcium sulfate dihydrate and transition metal salts, such as ferrous sulfate heptahydrate. The concentrations of each of the salts employed is generally between 0.1% and 20% of the starting organic compound or compounds on a molar basis. Preferably, a molar concentration of salt which is 0.2% to 10% of the molar concentration of the starting organic compound or compounds is employed. Most preferably, a molar concentration of salt which is 0.2% to 2% of the molar concentration of the starting organic compound or compounds, is employed. The exact concentration to be used can be determined by conventional synthetic yield optimization techniques.

The solution resulting from step E) is allowed to stand at room temperature with or without stirring for a period of time from 2 to 48 hours in step F). Any precipitate formed at this stage is removed via conventional centrifugation.

Molecules are removed from the solution resulting from step F) below about 500 to about 10,000 daltons in step G). A variety of known conventional techniques can be employed such as preparative chromatography, ultrafiltration or dialysis. Molecules are preferably removed from the solution resulting from step F) by employing dialysis in step G) with a flow-through open-channel or screen membrane apparatus consisting of a sandwich-type membrane of lower molecular-weight cutoff of 500–10,000 daltons until the conductivity of the solution has dropped to 200 microsiemens or less. Most preferably, molecules are removed from the solution resulting from step F) by employing dialysis in step G) until the conductivity of the solution has dropped to 30 microsiemens or less. A Pall Filtron Ultrasette® Tangential Flow Device or Mini- Ultrasette® Tangential Flow Device used with a Pall Filtron Ultralab® Specialized Pump and Reservoir System are preferred for solution dialysis.

The conductivity of the solution processed in step G) above can conveniently be monitored with a flow-through conductivity cell and conductivity meter. Alternatively, a simple inexpensive hand-held combination conductivity cell-conductivity meter (e.g., a Nalcometer Model MLN) can be employed.

Before removing the water from the solution in step H) above, the solution resulting from step G) above can be further dialyzed with a flow-through apparatus consisting of a sandwich-type membrane of molecular weight cutoff of 50,000 daltons. In this case the filtrate solution, not the retentate, is saved for further concentrating and processing according to steps H) and I). The resultant product will have a molecular-weight range of 500–50,000 daltons.

If the solution resulting from either steps G) or H) above is to be stored as an aqueous solution for long periods of time for later application or use, for example as an anti-viral treatment solution, anti-viral therapy, anti-microbial therapy, a spray-on fertilizer or soil amendment, it can be filtered through standard 0.2 to 0.4 micron filters to remove bacteria and viruses, that is, can be made sterile by filtration. Alternatively, the aqueous solution from either steps G) or H) can be autoclaved for 5–60 minutes at 100–150° C. to produce a sterile solution.

A final optional step I) in the process of the present invention involves removing water from the solution resulting from step H). When freeze-drying is employed as the method of water removal in step I) above, the resultant product is a light fluffy dark-colored powder that is subject to static electricity effects. To minimize these effects, a small amount of mannose or other sugar can be added to the solution resulting from step H) just prior to freeze-drying. Water removal from the product can be carried out by means other than freeze-drying in step I) above, such as by heat evaporation with or without vacuum, by rotary evaporation, by spray-drying, or by any other solvent-removal technique that is convenient as well as economical for aqueous solutions. The dried powder obtained from step I) above can be autoclaved for 15–30 minutes at 100–120° C. to produce a sterile powder.

The synthetic humic acid materials produced according to the chemical processes and separation and isolation procedures of the present invention exhibit the physicochemical properties and attributes of typical naturally-occurring commercially-available humic acids and other soil extracts.

A facile method of examining the physicochemical characteristics of the product yielded by steps A) through H) above, or by modifications thereto, is high-performance liquid chromatography (HPLC). The chromatographic fingerprint pattern so obtained from HPLC also offers a convenient means of comparing one product with another, as well as comparing each of the synthetic products with naturally-occurring humic acids and other soil-extract materials. The HPLC method is thus used to determine the reproducibility of the physiochemical properties and attributes of the synthetic phenolic polymeric materials, as well as to determine if the aforementioned properties and attributes simulate the physiochemical properties and attributes of typical commercial-available natural humic acids and other soil extracts. The latter determination of simulation is done in the conventional manner employing HPLC; e.g., by visually and quantitatively comparing the HPLC chromatographic fingerprint patterns of the materials. The fingerprint patterns of the two materials, one synthetic and one natural, need not be 100% identical to conclude that the physiochemical properties and attributes of the synthetic phenolic polymeric material simulates the physiochemical properties and attributes of the natural humic acid. An approximate correspondence between the aforementioned HPLC fingerprint patterns is all that is required to conclude that the synthetic material simulates the natural material. In general, even a 75% visual correspondence in 2 HPLC fingerprint patterns is all that is necessary to conclude that one material simulates another. A useful fingerprint pattern for natural as well as synthetic soil extract materials can be obtained as follows. The column is comprised of a packing, typically reversed-phase polymer PRP-1 (Hamilton Co.), of particle size 5 microns, and being 150 millimeters in length by 4.1 millimeters inside diameter. The mobile phase is comprised of three solutions. Solution A is 0.1 Normal aqueous sodium hydroxide. Solution B is 0.05 Normal of so-called Prideaux universal buffer, which is made by combining 4.25 grams of sodium nitrate ($NaNO_3$), 12.37 grams of boric acid ($H_3BO_3$), 23.06 grams of phosphoric acid ($H_3PO_4$), and 12.01 grams of acetic acid ($CH_3CO_2H$) with 4 liters of distilled water. Solution C is 100% methanol ($CH_3OH$). The mobile-phase gradient employed for an HPLC run consists of 40% solution A plus 60% solution B at the beginning, which composition is changed in a linear manner to 100% solution A after 20 minutes. The mobile phase is then changed linearly again to 10% A plus 90% C over the next 5 minutes, which final composition is held for the purpose of a column wash for the next 35 minutes. The mobile-phase flow rate is 1 milliliter per minute. The detector is UV-Visible, which is set at 340 nanometers. The chart speed is typically 0.5 centimeter per minute. The sample loop size is 5–20 microliters. Solutions are prepared for analysis by dissolving 1–10 grams of dried sample in 100 milliliters of 0.1 normal aqueous sodium hydroxide of pH 8–10.

The chemical processes and separation and isolation procedures of the present invention are suitable for scaleup directly to industrial levels that provide economically acceptable yields. The chemical processes and separation and isolation procedures of the present invention can produce synthetic product yields approaching 100%. More typically, approximately 0.08 to 0.65 g of synthetic humic acid can be produced from 10 millimoles of starting organic compound or compounds in 300 ml. These procedures can be scaled up to pharmaceutical production scales employing 10,000 to 20,000 liters or more of initial solution containing the starting organic compound or compounds. A total yield of between approximately 2.7 and 21.7 kg of synthetic humic acid can be achieved utilizing a 10,000 liter thermally jacketed stainless steel tank and a concentration of starting organic compound of 10 millimoles per 300 ml. A single anti-viral treatment may employ milligram amounts of synthetic humic acid. 20 kg of synthetic humic acid represents 2 million units of anti-viral product at 10 mg per unit. Even at a treatment cost of $ 0.10 per unit, this represents $ 200,000 of synthetic humic acid. Since the starting organic compounds utilized in the present invention are relatively inexpensive, the synthesis yields of the chemical processes and separation and isolation procedures of the present invention are economically very acceptable.

Examples 1 through 9 are illustrative of the variety of starting organic compounds that can be employed in the process of the present invention. It was not considered necessary to carry out all steps of the process of the present invention to illustrate starting compound variety. More particularly, Examples 1 through 9 are illustrative of all steps of the process of the invention with the exception of step E).

EXAMPLE 1

Preparation of a synthetic humic acid from 2,5-dihydroxybenzoic acid (gentisic acid). The starting organic compound is shown in Table 1, and consists of $R_1$=—$CO_2H$, $R_2,R_5$=—OH, and $R_3,R_4,R_6$=—H. 1.55 grams (10 millimoles) of gentisic acid is dissolved in 300 milliliters of 0.1 Normal aqueous sodium hydroxide (NaOH). The solution pH is adjusted to 8.5 with 6 Normal HCl. 0.54 gram of sodium periodate ($NaIO_4$; 2.5 millimoles) is added, and the solution is placed in a water-bath at 50° C. for 30 minutes. The solution is allowed to stand at room temperature overnight. Any precipitate is removed by centrifugation. The solution is dialyzed with a 3,000-dalton cut-off flow-through open-channel or screen membrane system (Pall Filtron: Ultrasette® 7 Tangential Flow Device or Mini-Ultrasette® 7 Tangential Flow Device used with a Pall Filtron Ultralab® 7 Specialized Pump and Reservoir System) to a conductivity of 30 microsiemens or less against distilled water. The dialysis apparatus is then used to concentrate the solution to about 200 milliliters. The solution can be saved at this point for further use as an aqueous solution; or it can be freeze-dried to a powder. (0.05–0.2 gram of mannose or other suitable carbohydrate can be added to the solution prior to freeze-drying to reduce static electricity effects associated with the freeze-dried powder.) The yield of synthetic soil extract is 0.2 gram.

The following examples 2–9 employ the synthesis procedure of Example 1 beginning with the adjustment of solution pH.

EXAMPLE 2

Preparation of a synthetic humic acid from 3,4-dihydroxyphenylacetic acid (homoprotocatechuic acid). The starting organic compound, 3,4-dihydroxy-phenylacetic acid, is shown in Table 1, and consists of $R_1$=—$CH_2CO_2H$, $R_3,R_4$=—OH, and $R_2,R_5,R_6$=—H. 1.68 grams (10 millimoles) of homoprotocatechuic acid is dissolved in 300 milliliters of 0.1 Normal aqueous sodium hydroxide (NaOH). The remaining procedure follows that of Example 1. The yield of synthetic soil extract is 0.24 gram.

EXAMPLE 3

Preparation of a synthetic humic acid from dl-(3,4-dihydroxyphenyl)hydroxyacetic acid (dl-3,4-dihydroxymandelic acid). The starting organic compound, dl-(3,4-dihydroxyphenyl)hydroxyacetic acid is shown in Table 1, and consists of $R_1$=—$CH(OH)CO_2H$, $R_3,R_4$=—OH, and $R_2,R_5,R_6$=—H. 1.84 grams (10 millimoles) of dl-3,4-dihydroxymandelic acid is dissolved in 300 milliliters of 0.1 Normal aqueous sodium hydroxide (NaOH). The remaining procedure follows that of Example 1. The yield of synthetic soil extract is 0.08 gram.

EXAMPLE 4

Preparation of a synthetic humic acid from aurintricarboxylic acid. The chemical structure of the starting organic compound is shown in Table 2. 4.2 grams (10 millimoles) of aurintricarboxylic acid is dissolved in 300 milliliters of 0.1 Normal aqueous sodium hydroxide (NaOH). The remaining procedure follows that of Example 1. The yield of synthetic soil extract is 4.7 grams.

EXAMPLE 5

Preparation of a synthetic humic acid from 3-(3,4-dihydroxyphenyl)propenoic acid (caffeic acid). The starting organic compound is shown in Table 1, and consists of $R_1$=—$CHCHCO_2H$, $R_3,R_4$=—OH, and $R_2,R_5,R_6$=—H. 1.80 grams (10 millimoles) of caffeic acid is dissolved in 300 milliliters of 0.1 Normal aqueous sodium hydroxide (NaOH). The remaining procedure follows that of Example 1. The yield of synthetic soil extract is 0.65 gram.

EXAMPLE 6

Preparation of a synthetic humic acid from tetrahydroxybenzoquinone. The chemical structure of the starting organic compound is shown in Table 2. 1.72 grams (10 millimoles) of tetrahydroxybenzoquinone is dissolved in 300 milliliters of 0.1 Normal aqueous sodium hydroxide (NaOH). The remaining procedure follows that of Example 1. The yield of synthetic soil extract is 0.016 gram.

EXAMPLE 7

Preparation of a synthetic humic acid from 1,4-dihydroxybenzene (hydroquinone). The starting organic compound is shown in Table 1, and consists of $R_1,R_4$=—OH, and $R_2,R_3,R_5,R_6$=—H. 1.10 grams (10 millimoles) of hydroquinone is dissolved in 300 milliliters of 0.1 Normal aqueous sodium hydroxide (NaOH). The remaining procedure follows that of Example 1. The yield of synthetic soil extract is 0.16 gram.

EXAMPLE 8

Preparation of a synthetic humic acid from 3,4,5-trihydroxybenzenoic acid (gallic acid). The starting organic compound is shown in Table 1, and consists of $R_1$=—CH2CO$_2$H, $R_3,R_4,R_5$=—OH, and $R_2,R_6$=—H. 1.70 grams (10 millimoles) of gallic acid is dissolved in 300 milliliters of 0.1 Normal aqueous sodium hydroxide (NaOH). The remaining procedure follows that of Example 1. The yield of synthetic soil extract is 0.10 gram.

EXAMPLE 9

Preparation of a synthetic humic acid from 2,5-dihydroxyphenylacetic acid (homogentisic acid). The starting organic compound is shown in Table 1, and consists of $R_1$=—CH$_2$CO$_2$H, $R_2,R_5$=—OH, and $R_3,R_4,R_6$=—H. 1.68 grams (10 millimoles) of homogentisic acid is dissolved in 300 milliliters of 0.1 Normal aqueous sodium hydroxide (NaOH). The remaining procedure follows that of Example 1. The yield of synthetic soil extract is 0.20 gram.

The following Examples 10–13 are illustrative of the entire process of the present invention including step E). Examples 10–13 illustrate that the synthetic humic acid materials produced according to the chemical processes and separation and isolation procedures of the present invention exhibit the physicochemical properties and attributes of typical naturally-occurring commercially-available humic acids and other soil extracts. Examples 10–13 also illustrate that the therapeutic indications of the synthetic humic acids produced according to the chemical processes and separation and isolation procedures of the present invention are those of soil extracts and humic acids in general, that is to say for viral-related and other disorders and diseases of inflammatory, microbial and other origin.

EXAMPLE 10

Figure 2:
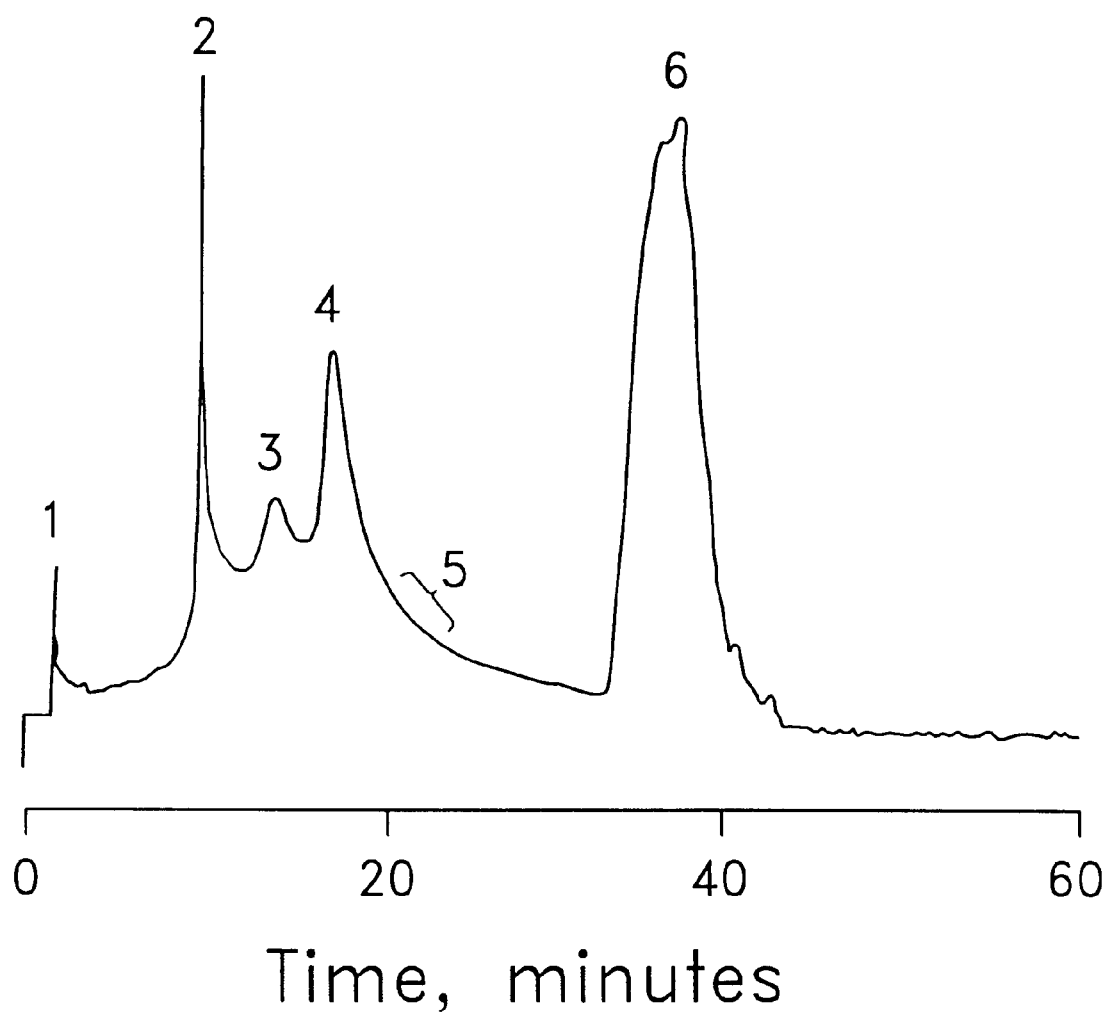
FIG. 2 shows the high-performance liquid chromatography (HPLC) trace obtained for a typical commercially-available natural humic acid.

Preparation of another synthetic humic acid from 2,5-dihydroxyphenylacetic acid (homogentisic acid). The starting organic compound is shown in Table 1, and consists of $R_1$=—CH$_2$CO$_2$H, $R_2,R_5$=—OH, and $R_3,R_4,R_5$=—H. 1.0 gram (6 millimoles) of homogentisic acid is dissolved in 300 milliliters of 0.1 Normal aqueous sodium hydroxide (NaOH). The solution pH is adjusted to 8.5 with 6 Normal HCl. 0.32 gram of sodium periodate (NaIO$_4$; 1.5 millimole) and 0.12 gram of sodium sulfide nonahydrate (Na$_2$S.9H$_2$O; 0.5 millimole) are added, and the solution is placed in a water-bath at 50° C. overnight. 0.001 gram of boric acid (H$_3$BO$_3$; 0.016 millimole), 0.021 gram of ferrous sulfate heptahydrate (FeSO$_4$.7H$_2$O; 0.075 millimole), and 0.006 gram of calcium sulfate dihydrate (CaSO$_4$.2H$_2$O; 0.035 millimole) are added and the solution is stirred for 2 hours at room temperature. Any precipitate is removed by centrifugation. The solution is dialyzed with a 3,000-dalton cut-off flow-through open-channel or screen membrane system (Pall Filtron: Ultrasette® 7 Tangential Flow Device or Mini-Ultrasette® 7 Tangential Flow Device used with a Pall Filtron Ultralab® 7 Specialized Pump and Reservoir System) to a conductivity of 30 microsiemens or less against distilled water. The dialysis apparatus is then used to concentrate the solution to about 200 milliliters. The solution can be saved at this point for further use as an aqueous solution; or it can be freeze-dried to a powder. (0.05–0.2 gram of mannose or other suitable carbohydrate can be added to the solution prior to freeze-drying to reduce static electricity effects associated with the freeze-dried powder.) The yield of synthetic soil extract is 0.23 gram. The HPLC trace of the synthetic soil extract obtained in this Example is illustrated in FIG. 1. Peaks 1–6 are produced by this example. Peak 5 is under the shoulder of Peak 4 and not overtly apparent. A mathematical first derivative of the detector signal versus time can more clearly show Peak 5. FIG. 2 shows the HPLC trace of a typical commercially-available natural humic acid. Peak 6 in FIGS. 1 and 2 is produced by a column wash with 90–100% v/v methanol and also contains synthetic humic acid. It can be seen that with the exception of the relative amounts of material in Peaks 2,4 and 6, the remainder of the HPLC traces in FIGS. 1 and 2 are essentially equivalent. Thus, the synthetic procedure of the present invention produced a humic acid material with physicochemical characteristics that are essentially equivalent to those of a commercially-available soil extract.

EXAMPLE 11

Preparation of still another synthetic humic acid from 2,5-dihydroxyphenylacetic acid (homogentisic acid). The starting organic compound is shown in Table 1, and consists of $R_1$=—CH$_2$CO$_2$H, $R_2,R_5$=—OH, and $R_3,R_4,R_6$=—H. 1.68 gram (10 millimoles) of homogentisic acid is dissolved in 300 milliliters of 0.1 Normal aqueous sodium hydroxide (NaOH). The solution pH is adjusted to 8.5 with 6 Normal HCl. 0.75 gram of sodium periodate (NaIO$_4$; 3.5 millimoles) and 0.24 gram of sodium sulfide nonahydrate (Na$_2$S.9H$_2$O; 1 millimole) are added, and the solution is placed in a water-bath at 50° C. overnight. 0.006 gram of boric acid (H$_3$BO$_3$; 0.1 millimole), 0.28 gram of ferrous sulfate heptahydrate (FeSO$_4$.7H$_2$O; 1 millimole), and 0.017 gram of calcium sulfate dihydrate (CaSO$_4$.2H$_2$O; 0.1 millimole) are added and the solution is stirred for 48 hours at room temperature. Any precipitate is removed by centrifugation. The solution is dialyzed with a 3,000-dalton cut-off flow-through open-channel or screen membrane system (Pall Filtron: Ultrasette™ 7 Tangential Flow Device or Mini-Ultrasette™ 7 Tangential Flow Device used with a Pall Filtron Ultralab™ 7 Specialized Pump and Reservoir System). The dialysis apparatus is then used to concentrate the solution to about 200 milliliters. The solution can be saved at this point for further use as an aqueous solution; or it can be freeze-dried to a powder. (0.05–0.2 gram of mannose or other suitable carbohydrate can be added to the solution prior to freeze-drying to reduce static electricity effects associated with the freeze-dried powder.) The yield of synthetic soil extract is 0.47 gram. The HPLC trace of the synthetic soil extract obtained in this Example is identical to that described in Example 10 and illustrated in FIG. 1.

EXAMPLE 12

Anti-viral properties of synthetic humic acid prepared according to Examples 10 and 11. Several hundred milligrams of synthetic humic acid are prepared according to the procedures of Examples 10 and 11. The antiviral properties of these materials was assessed according to the following methods:

Jurkat cells obtained from the American Type Culture Collection (Rockville, Md.) are subcultured every fifth day using RPMI-1640 medium supplemented with 2 millimolar L-glutamine and 15 percent by volume fetal bovine serum (FBS). Cell counts are determined with a Coulter particle counter (Coulter Corporation, Hialeah, Fla.). The cells are infected with an HIV-1 plasmid construct, pNL4-3 (A. Adachi, H. E. Gendleman, S. Koenig, T. Folks, R. Willey, A. Rabson, and M. A. Martin, *J. Virol.* 1986, 59, 284–291; cell cultures thereby treated produce high levels of HIV-1, approximately $1 \times 10^7$ particles per milliliter, as measured by electron microscopy). The infected cells are then cultured in complete medium comprised of RPMI-1640 supplemented with 2 millimolar L-glutamine, 15 percent by volume fetal calf serum, and 1 percent by volume Pen-Strep (100 Units of Penicillin and 100 milligrams of Streptomycin per milliliter). The cells are monitored for approximately four weeks prior to use in order to ensure stable HIV-1 production.

Prior to testing the anti-viral efficacy of the synthetic humic acid, Jurkat cell culture supernatants are first tested for HIV-1 p24 production to establish a pretreatment baseline. After confirming the level of virus production, the growth medium is changed and the cell number is adjusted to $1.5 \times 10^6$ cells per milliliter. Then, two days prior to administering the synthetic humic acid to be tested, equal volumes of transfected cells are admixed with normal, untreated cells to bring the level of virus production to within the range of the HIV-1 p24 immunoassay. After 24 hours, a known quantity of synthetic humic acid is added to the cell blend. The determination of HIV-1 p24 expression after a given number of days following synthetic humic acid administration is carried out with a solid-phase assay designed for HIV-1 antigens (HIVAG-1; Abbott Laboratories, Diagnostic Division, Abbott Park, Ill.; Abbott Quantum II ELISA reader and data reduction module 1.21).

Figure 3:
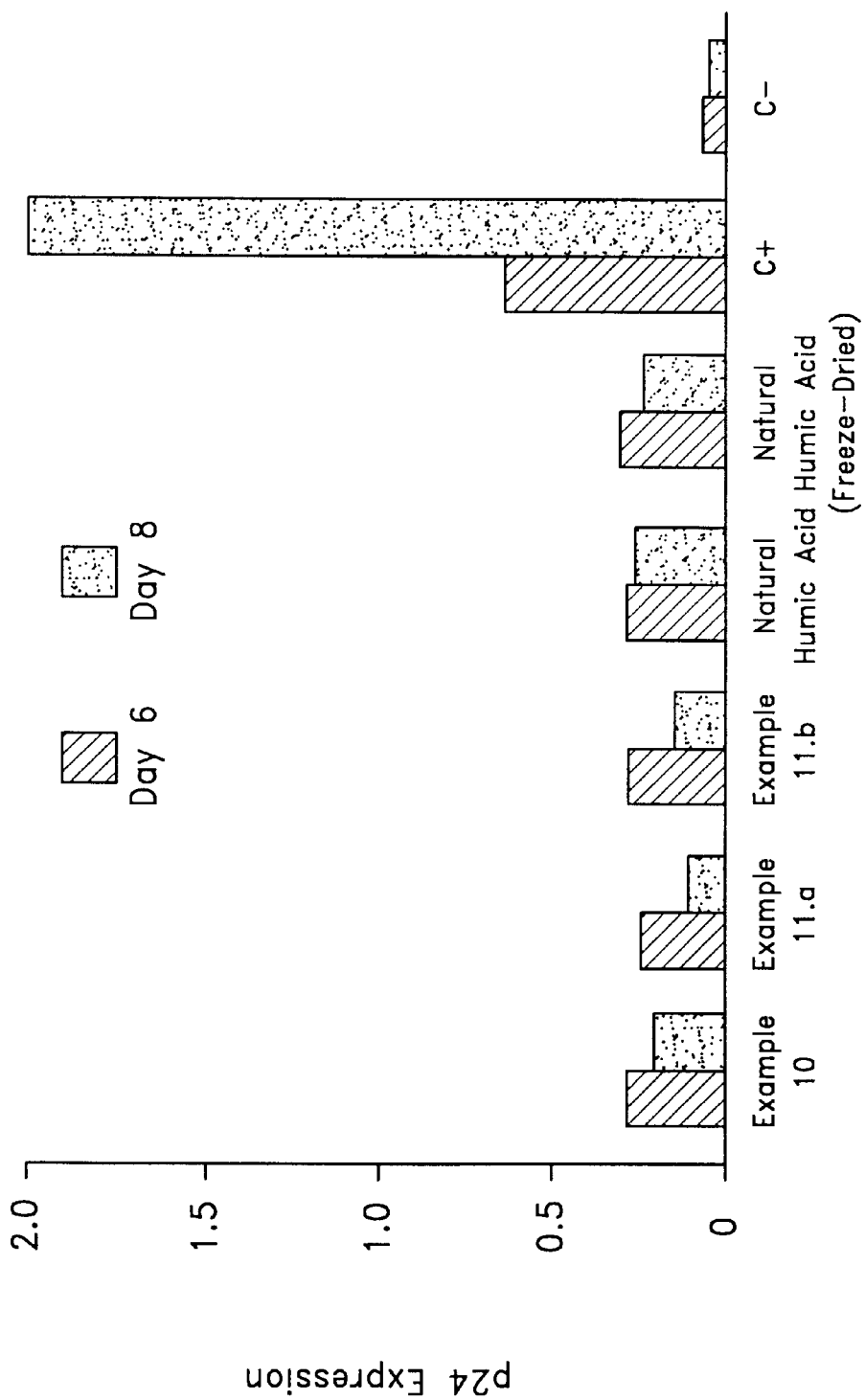
FIG. 3 shows the p24 expression of HIV-positive cells harvested 6 and 8 days after treatment with synthetic humic acids prepared as described in Examples 10 and 11. Also shown for comparison are the results obtained for natural humic acid that has been dialyzed, and natural humic acid that has been dialyzed and freeze-dried. C+ and C− are positive and negative controls, respectively.

FIG. 3 shows the effect of the synthetic humic acid prepared as described in Examples 10 and 11 on the p24 expression of HIV-positive cells as measured according to the procedures of Example 12. Example 11a in FIG. 3 was prepared exactly according to the procedure of Example 11. Example 11b in FIG. 3 was prepared according to the procedure of Example 11 with the additional step of freeze-drying the final solution. Shown for comparison are the results obtained with natural humic acid that was subjected to dialysis as described in Examples 1–11; and natural humic acid that was subjected to dialysis with subsequent freeze-drying as described in Examples 1-11. The results show significant reductions in p24 expression for all samples. Additionally, at day 12, no p24 was detected within the experimental error of the method ( none greater than the C–control ).

EXAMPLE 13

Toxicity of synthetic humic acid prepared according to Example 10. Several hundred milligrams of synthetic humic acid are prepared according to the procedure of Example 10. Five units of 450 milliliters each of whole human blood are collected into CP2D/AS-3 Leukotrap RC-PL systems. The blood is rested for 3 hours at room temperature. Each sample is weighed, and then centrifuged at 2820 revolutions per minute (2312 gravities) for 3 minutes, 44 seconds. The blood samples are then expressed through ATS-LPL filters into platelet storage bags. The filtration time is noted. The LR-PRP is centrifuged at 3600 revolutions per minute (3768 gravities) for 7 minutes. All but about 55 grams of platelet poor plasma is removed from each sample. The platelet concentrates are rested for 90 minutes at room temperature, and are then weighed and placed in a platelet incubator. RCM1 filters are primed with AS-3 solution. The primary bags are hung at a height of 60 inches above empty AS-3 bags, such that filtration occurs by gravity. The filtration time is noted, and the LR-RCC systems are sealed off 3 inches below the RCM1 filters. Each RCM1 filter together with 6 inches of tubing and the LR-RCC, including the donor identification tube segment, are weighed. Samples are taken at this point for post-filtration testing (LR-RCC). At day 1 sufficient synthetic humic acid is added to each platelet concentrate so as to make its concentration 25 micrograms per milliliter. Treated platelet concentrates are then incubated in a platelet incubator for 1 hour, following which samples of each platelet concentrate are taken for testing. Subsequent samples are also taken on day 5 for further testing.

Table 3 shows the effect of the synthetic humic acid prepared as described in Example 10 on the viability of platelet concentrates as measured according to the procedures of this Example. The results are all nominal, that is, the synthetic humic acid has no effect on platelet viability (i.e., is nontoxic). These results are particularly noteworthy, as blood platelets are known to be sensitive to a variety of chemical agents. It is for this reason that few safe anti-viral treatments are available for blood platelets.

Examples 12 and 13 illustrate that synthetic humic acids prepared according to the above processes and separation and isolation procedures of the present invention can be combined in anti-viral amounts with blood products to form blood product compositions. Synthetic humic acids may be added in anti-viral amounts to human or animal blood products such as whole blood, blood plasma, blood platelets or other blood products containing blood fractions such as haemophilia factor VIII, haemophilia factors IX and V, albumin, IgG, IgM or other blood proteins or blood materials to reduce or eliminate viral activity. Synthetic humic acids may be added in anti-viral amounts to both liquid and solid blood products. Synthetic humic acid will have application to blood materials including all blood materials where the solvent/detergent (SD) treatment applies. In direct contrast to the SD treatment, which is ineffective for nonenveloped viruses, synthetic humic acid prepared according to the present invention has anti-viral activity against both lipid enveloped and nonenveloped viruses and thus has broader application. An anti-viral amount of synthetic humic acid is an amount that is known from the prior art regarding anti-viral amounts of humic acids to be useful in reducing or eliminating viral activity. Generally, an anti-viral amount useful in blood product compositions for reducing or eliminating viral activity in liquid blood product compositions is a concentration of synthetic humic acid

TABLE 3

| Unit No. | pH at 22° C. | | pCO$_2$, mm Hg | | pO$_2$, mm Hg | | HCO3, mmol/L | | MPV, fl | |
|---|---|---|---|---|---|---|---|---|---|---|
| | Day 1 | Day 5 | Day 1 | Day 5 | Day 1 | Day 5 | Day 1 | Day 5 | Day 1 | Day 5 |
| 1 | 7.466 | 7.394 | 19.3 | 12.8 | 33.5 | 44.4 | 16.8 | 9.5 | 7.0 | 6.6 |
| 2 | 7.321 | 7.215 | 21.6 | 14.3 | 9.9 | 22.2 | 13.8 | 7.3 | 6.7 | 6.3 |
| 3 | 7.320 | 7.276 | 24.4 | 16.6 | 10.3 | 21.3 | 15.6 | 9.7 | 6.7 | 6.5 |
| 4 | 7.368 | 7.308 | 20.7 | 14.3 | 13.4 | 22.2 | 14.6 | 8.9 | 6.5 | 6.3 |
| 5 | 7.457 | 7.454 | 20.1 | 13.8 | 23.7 | 29.0 | 17.1 | 11.6 | 7.7 | 7.4 |
| Mean | 7.386 | 7.329 | 21.2 | 14.4 | 18.2 | 27.8 | 15.6 | 9.4 | 6.9 | 6.6 |
| Std. Dev. | 0.071 | 0.095 | 2.0 | 1.4 | 10.2 | 9.8 | 1.4 | 1.5 | 0.5 | 0.6 |

| Unit No. | WBC Yield, ×10$^5$ | Platelet Yield, ×10$^{10}$ | | Streaming | | % ESC | | % HSR | | Lactate, mmol/L | |
|---|---|---|---|---|---|---|---|---|---|---|---|
| | Day 1 | Day 1 | Day 5 | Day 1 | Day 5 | Day 1 | Day 5 | Day 1 | Day 5 | Day 1 | Day 5 |
| 1 | 0.1 | 8.3 | 9.0 | 3 | 3 | 24.2 | 16.9 | 78.0 | 64.0 | 5.1 | 12.1 |
| 2 | 0.2 | 14.5 | 14.2 | 3 | 3 | 27.5 | 20.3 | 81.7 | 71.5 | 6.6 | 13.4 |
| 3 | 0.4 | 13.3 | 13.4 | 3 | 3 | 28.7 | 26.3 | 81.7 | 79.4 | 6.3 | 12.4 |
| 4 | 0.3 | 11.7 | 12.3 | 3 | 2 | 22.1 | 19.2 | 81.4 | 77.1 | 6.6 | 13.1 |
| 5 | 0.3 | 8.9 | 9.1 | 3 | 3 | 19.1 | 14.4 | 74.7 | 70.2 | 4.5 | 9.7 |
| Mean | 0.3 | 11.3 | 11.6 | 3.0 | 2.8 | 24.3 | 19.4 | 79.5 | 72.4 | 5.8 | 12.1 |
| Std. Dev. | 0.1 | 2.7 | 2.4 | 0.0 | 0.4 | 3.9 | 4.5 | 3.1 | 6.1 | 1.0 | 1.4 | between 5 and 1000 micrograms per milliliter of liquid blood product composition. This same concentration range applies to solid blood product compositions containing dried synthetic humic acid upon dissolution in solution prior to use. The exact amount to be utilized to reduce or eliminate viral activity depends upon the particular virus and blood product and can be determined with conventional anti-viral test procedures known in the art. Whole blood, blood plasma or other blood products suspected to be contaminated or contaminated with HIV or hepatitis virus can be modified, for example, with the addition of about 10 to about 200 micrograms per milliter of synthetic humic acid. Examples 14 and 15 are illustrative of blood product compositions containing anti-viral amounts of synthetic humic acid prepared according to the processes and separation and isolation procedures of the present invention.

EXAMPLE 14

Whole human blood composition containing 25 ug/milliliter of a synthetic humic acid from 2,5-dihydroxyphenylacetic acid (homogentisic acid). The blood product composition follows:

Whole human blood: 1 liter

Synthetic humic acid: 25 mg

EXAMPLE 15

Human haemophilia factor VIII composition containing a synthetic humic acid from 2,5-dihydroxyphenylacetic acid (homogentisic acid). The blood product composition follows:

Human haemophilia factor VIII: 1–5 ml vial*

Synthetic humic acid: 125 ug

*Note: This is a vial containing sterile highly purified lyophilized factor VIII concentrate intended for dilution with 5ml of sterile injectable saline and containing 3900 units (IU) of factor VIII at a concentration of 100 IU/mg of protein.

Synthetic humic acids prepared according to the above processes and separation and isolation procedures of the present invention can be utilized in anti-viral amounts as defined above in methods for reducing or eliminating the amount of virus in human or animal blood products. Generally, such methods involve contacting the blood product in some way with an anti-viral amount of synthetic humic acid. Various means of contacting can be employed, such as direct injection of a sterile solution containing said anti-viral amount into said blood product. A particularly preferred method involves the usage of so-called "dual bag" technology for intravenous solutions. This method employs a plastic bag with two separate chambers and a connecting path between them. The two chambers may vary in volume and the volume ratio between them. The two chambers may contain two different drugs or for the purpose of employing the present invention, a blood product in one chamber and the synthetic humic acid in the other chamber. The connecting path is closed until the product is ready to be used. The path can be opened with a valve arrangement or by breaking a seal between the two chambers. The seal is typically broken without compromising the sterility of the products in both chambers. Dual bag sterile solution technology is available from Abbott Laboratories in Illinois, McGaw in California and other companies. Alternatively, a blood product may be contacted with an anti-viral amount of synthetic humic acid during the processing of the blood product prior to or including the final processing step wherein the blood product is placed into its final container for patient use. Due to the nontoxic nature of synthetic humic acid as prepared herein, it is not necessary to separate the humic acid from the blood product prior to use of the blood product. It has already been disclosed herein that it is necessary to separate the detergents in the solvent/detergent (SD) blood treatment method from the blood product utilizing extraction with soybean or castor oil and chromatography on insolubilized C18 resin. Methods for reducing or eliminating the amount of virus in human blood products employing synthetic humic acid have an additional advantage over the SD methods in that unlike the SD methods, both lipid enveloped and nonenveloped viruses can be inactivated. Additionally, unlike various heat treatments or ultraviolet light irradiation of blood products, essentially no loss of blood product is observed with synthetic humic acid treatment methods. Methods for reducing or eliminating the amount of virus in blood products employing synthetic humic acid can be combined with the solvent/detergent (SD) blood treatment method or other blood treatment methods, including heat treatments, ultraviolet irradiation or other methods. One or more of the aforementioned blood treatment methods may be combined with the humic acid treatment method.

Example 16 illustrates that synthetic humic acids prepared according to the above processes and separation and isolation procedures of the present invention can be utilized in anti-viral amounts in methods for reducing the amount of virus in human blood products.

EXAMPLE 16

Method for the reduction of the amount of virus in human blood bags with the use of synthetic humic acid from 2,5-dihydroxyphenylacetic acid (homogentisic acid). The antiviral properties of the synthetic humic acid material prepared according to the procedure of Example 10 are assessed according to the following methods: In this example, Bovine Viral Diarrhea Virus (BVDV) is utilized as an indicator virus for anti-viral activity. BVDV is a lipid-enveloped virus and is known to be a good indicator virus for anti-viral activity, including anti-human immunodeficiency virus activity. A titered virus stock of BVDV at a TCID 50 of 10E-7 is prepared. Twelve blood bags containing blood platelets are obtained (one for each humic acid concentration, 0,10,50 and 100 ug/ml, performed in triplicate). The method for the reduction of the amount of virus in human blood bags with the use of synthetic humic acid involves a simple addition of a sterile volumetric amount of synthetic humic acid in aqueous solution to each blood bag. Specifically, a sterile liquid aliquot of a 100 ug/ml concentration of synthetic humic acid in distilled water is added to each blood bag containing between 40 and 60 ml of blood product such that the final concentration of humic acid was 10, 50 or 100 ug/ml. Bags are sampled at the following intervals: T0 hours as a pre-inoculation control; T1 hour post inoculation with the virus stock (at T1 hour post inoculation the humic acid is added); at T2 hours post inoculation another sample is pulled. Additional samples are pulled at T24 hours, T72 hours and T120 hours. Quantitative virus cultures are prepared from the pulled samples and the resulting TCID 50s and log reductions are determined for each humic acid concentration. The results of the testing show that synthetic humic acid prepared according to the present invention can successfully be used in methods for reducing the amount of virus in human blood products.

Synthetic humic acid prepared according to the above processes and separation and isolation procedures of the present invention can be utilized in anti-viral amounts in compositions for treating or preventing human or animal viral diseases. Synthetic humic acid containing compositions are suitable for treating or preventing human or animal viral diseases for which natural humic acid materials have been shown to be useful. Thus, synthetic humic acid compositions are suitable for treating or preventing human disease caused by Human Immunodeficiency Virus (HIV), Herpes Simplex Virus and other human viruses. Synthetic humic acid compositions are also suitable for treating or preventing diseases caused by the entire picornavirus family including the current five known genera of viruses: (1) aphthoviruses, (2) cardioviruses, (3) hepatoviruses (previously classified as enteroviruses), (4) renteroviruses (which mainly constitute a combination of the previous genera rhinovirus and enterovirus), and (5) a new genus, with a single representative to date, the echovirus 22. Compositions suitable for various routes of administration and particular viral diseases can be prepared. An anti-viral amount of synthetic humic acid for a particular viral disease can be determined from the known anti-viral amount of natural humic acid known to be useful for the same particular viral disease. A variety of compositions comprising an anti-viral amount of synthetic humic acid and at least one physiologically acceptable excipient can be prepared. Compositions comprising physiologically acceptable excipients suitable for intravenous injection, intramuscular injection, topical application, oral ingestion, nasal spray administration, metered-dose inhalation administration and vaginal and anal suppository administration can be prepared with known excipients and methods. Examples 17–21 are illustrative of the foregoing compositions.

EXAMPLE 17

Injectible solution composition for treating human immunodeficiency virus (HIV) infection containing an anti-viral amount of synthetic humic acid from 2,5-dihydroxyphenylacetic acid (homogentisic acid) and injectable solution excipients:

| | |
|---|---|
| Sodium chloride | 9.00 gram |
| Synthetic humic acid | 500 mg |
| Distilled water | q.s. to 1 liter |

The pH of the above solution can additionally be adjusted to 7.4 with 1 Normal sodium hydroxide prior to adding all of the water. This injectable solution composition can be prepared by conventional methods for preparing injectable sterile solutions.

EXAMPLE 18

Topical ointment composition for treating human herpes simplex virus (HSV-I or HSV-II) infection containing an anti-viral amount of synthetic humic acid from 2,5-dihydroxyphenylacetic acid (homogentisic acid) and topical formulation excipients:

| | |
|---|---|
| Synthetic humic acid | 3.0 gram |
| Cetostearyl alcohol | 27 gram |
| Liquid paraffin | 20 gram |
| White soft paraffin | 50 gram |

EXAMPLE 19

Topical cream composition for treating human herpes simplex virus (HSV-I or HSV-II) infection containing an anti-viral amount of synthetic humic acid from 2,5-dihydroxyphenylacetic acid (homogentisic acid) and topical formulation excipients:

| | |
|---|---|
| Synthetic humic acid | 2.4 gram |
| Cetosteryl alcohol | 5 gram |
| Liquid paraffin | 50 gram |
| Distilled water | add to 100 gram |

EXAMPLE 20

Topical solution composition for treating human herpes simplex virus (HSV-I or HSV-II) infection containing an anti-viral amount of synthetic humic acid from 2,5-dihydroxyphenylacetic acid (homogentisic acid) and topical formulation excipients:

| | |
|---|---|
| Synthetic humic acid | 2.4 gram |
| Sodium sulfide | 1.0 gram |
| Colloidal sulfur | 1.4 gram |
| Sodium chloride | 2.2 gram |
| Potassium sorbate | 0.2 gram |

Distilled water q.s. to 100 ml

Note that the above composition contains the same amount of humic acid disclosed by Wagner in German patent DE 3830333.

EXAMPLE 21

Ingestible lozenge composition for treating human immunodeficiency virus (HIV) infection containing an anti-viral amount of synthetic humic acid from 2,5-dihydroxyphenylacetic acid (homogentisic acid) and ingestible lozenge excipients:

| | |
|---|---|
| Synthetic humic acid | 500 mg |
| Menthol | 3.6 mg |
| Cetylpyridinium chloride | 1.4 mg |
| Cherry flavor | 100 mg |
| Glucose | 500 mg |
| Sucrose | 500 mg |

Other excipients may also be added to the above composition. Colorants such as D&C Red No. 33, FD&C Red No. 40 or other colorants may be used. Other flavoring agents may also be utilized in lozenge formulations as well preservatives other than cetylpyridinium chloride. The aforementioned excipients as well as other excipients not mentioned are all known in the art and can be employed in amounts previously used in lozenge formulas. The composition of Example 21 is also useful for treating the common cold, which is caused by members of the rhinovirus family. Nasal spray compositions containing synthetic humic acid are also particularly useful for treating the common cold.

Compositions comprising physiologically acceptable excipients suitable for disinfection and preservation of medical devices can be prepared with known excipients and methods. A variety of medical devices which contact the body can be disinfected or preserved with compositions containing synthetic humic acid. These medical devices can be disinfected or preserved before or after bodily contact to prevent viral infection. Contact lenses, intraocular lenses, dental prostheses, implantable medical devices such as heart valves and medical instruments which contact the body such as endoscopes and catheters can be disinfected or preserved with compositions containing synthetic humic acid.

Synthetic humic acid prepared according to the above processes and separation and isolation procedures of the present invention can be utilized in anti-microbial amounts in compositions for treating or preventing human or animal microbial diseases. An anti-microbial amount of synthetic humic acid is an amount that is known from the prior art referenced herein regarding anti-microbial amounts of humic acids to be useful in reducing or eliminating microbial activity. Generally, an anti-microbial amount useful in product compositions for reducing or eliminating microbial activity in liquid product compositions is a concentration of synthetic humic acid between 50 and 2000 micrograms per milliliter of liquid product composition. This same concentration range applies to solid product compositions containing dried synthetic humic acid upon dissolution in solution prior to use. Cronje et al., U.S. Pat. No. 4,999,202, discloses bacteriocidal or bacteriostatic compositions comprising humic acid with higher concentrations. The concentrations employed by Cronje et al. can also be employed herein. The exact amount to be utilized to reduce or eliminate microbial activity depends upon the particular microorganism and product and can be determined with conventional anti-microbial test procedures known in the art. The synthetic humic acids of the present invention have anti-microbial activity comparable to the activity of natural humic acids and other synthetic humic acids referenced herein. Thus, the synthetic humic acids of the present invention will have activity against cryptosporidium species, C.albicans, Ent. cloacae, Prot. vulgaris, Ps. aeruginosa, S. typhimurium, St. aureus, St. epidermidis, Str. pyrogenes, Str. mutans, E. coli and other organisms. A variety of compositions comprising an anti-microbial amount of synthetic humic acid and at least one physiologically acceptable excipient can be prepared. Compositions comprising physiologically acceptable excipients suitable for intravenous injection, intramuscular injection, topical application, oral ingestion, nasal spray administration, metered-dose inhalation administration and vaginal and anal suppository administration can be prepared with known excipients and methods. The topical compositions of Examples 18–20 also have anti-microbial activity and are illustrative of anti-microbial compositions. Compositions comprising physiologically acceptable excipients suitable for disinfection and preservation of medical devices such as contact lenses can be prepared with known excipients and methods. A variety of medical devices which contact the body can be disinfected or preserved with compositions containing synthetic humic acid. These medical devices can be disinfected or preserved before or after bodily contact to prevent microbial infection. Contact lenses, intraocular lenses, dental prostheses, implantable medical devices such as heart valves and medical instruments which contact the body such as endoscopes and catheters can be disinfected or preserved with compositions containing synthetic humic acid. Example 22 which follows is illustrative of a composition suitable for disinfection and preservation of contact lenses. Example 22 is illustrative of a one bottle contact lens multipurpose disinfecting, preservation (storage), cleaning, rinsing and rewetting solution. This solution provides the necessary antibacterial disinfection activity required by U.S. FDA disinfection efficacy guidelines for contact lens solutions. This solution is non-toxic and extremely comfortable for the eye and thus can be placed directly in the contact lens user's eye without further rinsing with a separate saline solution. The solution can be used with all contact lenses such as conventional hard, soft, rigid, gas permeable and silicone lenses but is preferably employed with soft lenses such as those commonly referred to as hydrogel lenses prepared from monomers such as hydroxyethylmethacrylate, vinylpyrrolidone, glycerolmethacrylate, methacrylic acid or acid esters and the like. Proteolytic enzymes used for cleaning contact lenses, such as those disclosed in U.S. Pat. No. 5,356,555 can also be combined with contact lens multipurpose solutions containing synthetic humic acid prepared according to the methods of the present invention. The methods of combining proteolytic enzymes with synthetic humic acid containing multipurpose solutions and the amounts of enzyme and excipients to be employed are the same as disclosed in U.S. Pat. No. 5,356,555 which is incorporated herein by reference. Generally, for the purposes of the present invention an aqueous solution containing from 0.0010 w/v % to less than or equal to 0.0100 w/v % of the synthetic humic acid disinfecting agent may be used as a contact lens multipurpose solution. Contact lens multipurpose solutions containing synthetic humic acid prepared according to the methods of the present invention have advantages over the prior art contact lens multipurpose solutions containing other disinfecting agents. Synthetic humic acid containing multipurpose solutions achieve equal or greater disinfection efficacy while providing greater comfort for the contact lens wearer. This is a result of the inherently lower cytotoxicity or toxicity of synthetic humic acid disinfecting agents as compared to prior art disinfecting agents which are presently in use for contact lens multipurpose solutions. The advantages of synthetic humic acid for contact lens applications are also a result of their anionic and neutral polymeric nature. Current contact lens multipurpose solutions contain cationic polymeric disinfecting agents such as polyhexamethylenebiguanide (PHMB) and polyquaternium 1 which have a much higher affinity for the inherently neutral to anionic contact lens polymers. However, the synthetic humic acid prepared according to the present invention is a colored material. Solutions at a concentration of 0.0025 w/v % are very light brown. Thus, for cosmetic reasons, not all solutions may be acceptable. However, because they are neutral to anionic polymers, synthetic humic acid will have a low affinity for plastic materials and therefore the materials will not be discolored if the synthetic humic acid compositions are formulated properly.

EXAMPLE 22

One-bottle contact lens multipurpose disinfecting, preservation (storage), cleaning, rinsing and re-wetting solution containing an anti-microbial amount of synthetic humic acid from 2,5-dihydroxyphenylacetic acid (homogentisic acid). The aqueous solution has the following composition:

| Ingredient | % w/v |
| --- | --- |
| Synthetic humic acid | 0.0025 |
| Edetate disodium, USP | 0.050 |
| Hydroxypropylmethylcellulose | 0.20 |
| Boric acid, NF | 0.39 |
| Sodium borate decahydrate, NF | 0.20 |
| Sodium chloride, USP | 0.40 |
| Pluronic F-127 | 0.10 |
| pH adj. w/NaOH or HCl | 7.4 |

While this invention has been described fully and completely with special emphasis on several examples, it should be understood that within the scope of the appended claims this invention may be practiced otherwise than as specifically described above.

What is claimed is:

1. A composition for treating or protecting against infectious disease in a mammal comprising an effective amount of a synthetic phenolic polymeric material, said synthetic phenolic material having been prepared by the following steps:

a) dissolving in an aqueous solution at least one starting organic compound comprising at least one hydroxyl group and at least one carbonyl group or at least two hydroxyl groups on an aromatic structure;

b) adjusting the pH of the aqueous solution resulting from step a) to between about 8 and 11;

c) oxidizing the at least one starting organic compound solution resulting from step b);

d) polymerizing the oxidized compound resulting from step c);

e) adding at least one water soluble compound or salt selected from the group consisting of boric acid, borate salts, alkaline earth salts, transition metal salts, alkaline sulfides, alkaline earth sulfides, or transition metal sulfides to the aqueous solution resulting from step d); and f) removing molecules from the solution resulting from step e) below about 500 to about 10,000 daltons; and at least one physiologically acceptable carrier or excipient.

2. The composition of claim 1, wherein the synthetic polymeric material does not contain nitrogen.

3. The composition of claim 1, wherein the synthetic polymeric material is a synthetic fulvic acid.

4. The composition of claim 1, wherein the physiologically acceptable carrier or excipient is an injectable carrier or excipient.

5. The composition of claim 1, wherein the physiologically acceptable carrier or excipient is a topical formulation carrier or excipient.

6. The composition of claim 1, wherein the physiologically acceptable carrier or excipient is an ingestable carrier or excipient.

7. The composition of claim 1, wherein the physiologically acceptable carrier or excipient is a nasal spray carrier or excipient.

8. The composition of claim 1, wherein the physiologically acceptable carrier or excipient is a metered-dose inhaler carrier or excipient.

9. The composition of claim 1, wherein the physiologically acceptable carrier or excipient is a vaginal or anal suppository carrier or excipient.

10. The composition of claim 1, wherein the physiologically acceptable carrier or excipient is suitable for disinfection or preservation of a medical device.

11. A composition for treating or preventing infectious disease in a mammal comprising:

an effective amount of a synthetic phenolic polymeric material produced from the oxidation of one or more of the starting organic compounds selected from the group consisting of a compound represented by the formula I:

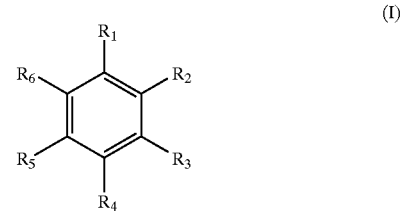

(I)

wherein $R_1, R_2, R_3, R_4, R_5$, and $R_6$ is a substituent selected from the group consisting of H, $CH_3$, $CH_2CH_3$, $(CH_2)_2CH_3$, $-CH(CH_3)_2$, OH, $-OCH_3$, CHO, $CO_2H$, $CO_2CH_3$, $CH_2OH$, $CH_2OCH_3$, $CH_2CHO$, $CH_2CO_2H$, $CH_2CO_2CH_3$, $(CH_2)_2OH$, $(CH_2)_2OCH_3$, $(CH_2)_2CHO$, $(CH_2)_2CO_2H$, $(CH_2)_2CO_2CH_3$, $CH(CH_3)OH$, $CH(CH_3)OCH_3$, $CH(CH_3)CHO$, $CH(CH_3)CO_2H$, $CH(CH_3)CO_2CH_3$, $CH(CH_3)CH_2OH$, $CH(CH_3)CH_2OCH_3$, $CH(CH_3)CH_2CHO$, $CH(CH_3)CH_2CO_2H$, $CH(CH_3)CH_2CO_2CH_3$, $CH(OH)_2$, $CH(OH)OCH_3$, $CH(OH)CHO$, $CH(OH)CO_2H$, $CH(OH)CO_2CH_3$, $CH(OCH_3)OH$, $CH(OCH_3)_2$, $CH(OCH_3)CHO$, $CH(OCH_3)CO_2H$, $CH(OCH_3)CO_2CH_3$, $CH(OH)CH_2OH$, $CH(OH)CH_2OCH_3$, $CH(OH)CH_2CHO$, $CH(OH)CH_2CO_2H$, $CH(OH)CH_2CO_2CH_3$, $CH(OCH_3)CH_2OH$, $CH(OCH_3)CH_2OCH_3$, $CH(OCH_3)CH_2CHO$, $CH(OCH_3)CH_2CO_2H$, $CH(OCH_3)CH_2CO_2CH_3$, $(CH_2)_3OH$, $—(CH_2)_3OCH_3$, $(CH_2)_3CHO$, $(CH_2)_3CO_2H$, $(CH_2)_3CO_2CH_3$, CHCHOH (cis or trans), $CHCHOCH_3$ (cis or trans), CHCHCHO (cis or trans), $CHCHCO_2H$ (cis or trans), $CHCHCO_2CH_3$ (cis or trans), $CH_2CHCHOH$ (cis or trans), $CH_2CHCHOCH_3$ (cis or trans), $CH_2CHCHCHO$ (cis or trans), $CH_2CHCHCO_2H$ (cis or trans), and $CH_2CHCHCO_2CH_3$ (cis or trans);

and an organic compound selected from the group consisting of nordihydroguaiaretic acid, chlorgenic acid, epinephrine, norepeinephrine, aurin, aurintricarboxylic acid, and tetrahydroxybenzoquinone;

in the presence of one or more water soluble compounds or salts selected from the group consisting of boric acid, borate salts, alkaline earth salts, transition metal salts, alkaline sulfides, alkaline earth sulfides and transition metal sulfides; and at least one physiologically acceptable carrier or excipient.

12. The composition of claim 11, wherein the starting organic compound contains at least one hydroxy group and at least one carboxylic acid group.

13. The composition of claim 11, wherein the physiologically acceptable carrier or excipient is an injectable carrier or excipient.

14. The composition of claim 11, wherein the physiologically acceptable carrier or excipient is a topical formulation carrier or excipient.

15. The composition of claim 11, wherein the physiologically acceptable carrier or excipient is an ingestable carrier or excipient.

16. The composition of claim 11, wherein the physiologically acceptable carrier or excipient is a nasal spray carrier or excipient.

17. The composition of claim 11, wherein the physiologically acceptable carrier or excipient is a metered-dose inhaler carrier or excipient.

18. The composition of claim 11, wherein the physiologically acceptable carrier or excipient is a vaginal or anal suppository carrier or excipient.

19. The composition of claim 11, wherein the physiologically acceptable carrier or excipient is suitable for disinfection or preservation of a medical device.

20. The composition of claim 1, wherein the steps to prepare the synthetic phenolic material does not include acid precipitation.

21. The method of claim 1, wherein the synthetic phenolic material has been prepared by a method wherein step c) comprises adding an alkaline periodate salt or alkaline-earth periodate salt to the aqueous solution resulting from step b).

22. The method of claim 1, wherein the synthetic phenolic material has been prepared by a method wherein step d) comprises maintaining the temperature of the solution from step c) between about 20° C. and 100° C. for a period of at least about 30 minutes.

23. The method of claim 1, the synthetic phenolic material has been prepared by a method further comprising allowing the aqueous solution from step e) to stand with or without stirring at about 20° C. to 100° C. for at least about 2 hours after step e).

* * * * *

UNITED STATES PATENT AND TRADEMARK OFFICE
CERTIFICATE OF CORRECTION

PATENT NO.      : 6,569,416 B1
DATED           : May 27, 2003
INVENTOR(S)     : Richard J. Laub It is certified that error appears in the above-identified patent and that said Letters Patent is hereby corrected as shown below:

<u>Title page,</u>
Item [73], Assignee, should read -- Laub --, rather the "Lamb"

Signed and Sealed this

Fourth Day of May, 2004

JON W. DUDAS
*Acting Director of the United States Patent and Trademark Office*